US012029799B2

(12) United States Patent
Hamersky et al.

(10) Patent No.: US 12,029,799 B2
(45) Date of Patent: *Jul. 9, 2024

(54) CONDITIONING HAIR CARE COMPOSITIONS IN THE FORM OF DISSOLVABLE SOLID STRUCTURES

(71) Applicant: The Procter & Gamble Company, Cincinnati, OH (US)

(72) Inventors: Mark William Hamersky, Hamilton, OH (US); Jennifer Elaine Hilvert, Cincinnati, OH (US); Emily Ann Lao, Cincinnati, OH (US); Jay Ryan Tenkman, Fairfield Township, OH (US); Stephen Robert Glassmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,390

(22) Filed: Apr. 27, 2022

(65) Prior Publication Data

US 2022/0257476 A1 Aug. 18, 2022

Related U.S. Application Data

(63) Continuation of application No. 15/979,961, filed on May 15, 2018, now Pat. No. 11,351,094.

(Continued)

(51) Int. Cl.
*A61K 8/02* (2006.01)
*A61K 8/34* (2006.01)
(Continued)

(52) U.S. Cl.
CPC ............ *A61K 8/0216* (2013.01); *A61K 8/342* (2013.01); *A61K 8/361* (2013.01); *A61K 8/37* (2013.01);
(Continued)

(58) Field of Classification Search
CPC .... A61K 8/0208; A61K 8/027; A61K 8/0216; A61K 8/8176; A61K 8/8158;
(Continued)

(56) References Cited

U.S. PATENT DOCUMENTS 1,421,350 A 6/1922 Powell
2,356,168 A 8/1944 Mabley
(Continued)

FOREIGN PATENT DOCUMENTS

AU 2004202461 B2 11/2007
CA 2300638 A1 8/2000
(Continued)

OTHER PUBLICATIONS

Afifi-Effat et al., Polymer Letters, 9: 651-655 (1971).
(Continued)

*Primary Examiner* — Hong Yu
(74) *Attorney, Agent, or Firm* — Alexandra S. Anoff

(57) ABSTRACT

The Dissolvable Solid Structure as described herein can be in the form of a fibrous structure comprising: (a) a polymeric structurant; (b) a high melting point fatty compound such as a fatty amphiphile, and (c) a cationic surfactant. The polymeric structurant has a weight average molecular weight of from about 10,000 to about 6,000,000 g/mol, and the components of the fibrous material form a homogenous material when molten. When water is added to the dissolvable solid structure at a ratio of about 5:1 a lamellar structure is formed.

19 Claims, 10 Drawing Sheets

Related U.S. Application Data

(60) Provisional application No. 62/506,777, filed on May 16, 2017.

(51) Int. Cl.
 *A61K 8/36*     (2006.01)
 *A61K 8/37*     (2006.01)
 *A61K 8/41*     (2006.01)
 *A61K 8/42*     (2006.01)
 *A61K 8/73*     (2006.01)
 *A61K 8/81*     (2006.01)
 *A61Q 5/12*     (2006.01)

(52) U.S. Cl.
 CPC ............... *A61K 8/41* (2013.01); *A61K 8/416* (2013.01); *A61K 8/42* (2013.01); *A61K 8/731* (2013.01); *A61K 8/8158* (2013.01); *A61K 8/8176* (2013.01); *A61Q 5/12* (2013.01)

(58) Field of Classification Search
 CPC . A61K 8/731; A61K 8/42; A61K 8/37; A61K 8/416; A61K 8/41; A61K 8/361; A61K 8/342; A61Q 5/12
 See application file for complete search history.

(56) References Cited

U.S. PATENT DOCUMENTS

| | | | |
|---|---|---|---|
| 2,396,278 | A | 3/1946 | Otto |
| 2,438,091 | A | 3/1948 | Lynch |
| 2,486,921 | A | 11/1949 | Byerly |
| 2,486,922 | A | 11/1949 | Bruce |
| 2,528,378 | A | 10/1950 | Mannheimer |
| 2,613,185 | A | 10/1952 | Marshall |
| 2,658,072 | A | 11/1953 | Milton |
| 2,694,668 | A | 11/1954 | Fricke |
| 2,809,971 | A | 10/1957 | Jack et al. |
| 3,152,046 | A | 10/1964 | Maria |
| 3,157,611 | A | 11/1964 | Lindemann |
| 3,236,733 | A | 2/1966 | Karsten et al. |
| 3,293,718 | A | 12/1966 | Melvin |
| 3,321,425 | A | 5/1967 | Karl-ludwig et al. |
| 3,332,880 | A | 7/1967 | Adriaan et al. |
| 3,426,440 | A | 2/1969 | Shen et al. |
| 3,428,478 | A | 2/1969 | Donaldson et al. |
| 3,463,308 | A | 8/1969 | Deneke |
| 3,489,688 | A | 1/1970 | Pospischil |
| 3,570,122 | A | 3/1971 | Willimas |
| 3,589,007 | A | 6/1971 | Walton |
| 3,653,383 | A | 4/1972 | Wise |
| 3,695,989 | A | 10/1972 | Albert |
| 3,753,196 | A | 8/1973 | Kurtz et al. |
| 3,761,418 | A | 9/1973 | Parran |
| 3,859,125 | A | 1/1975 | Miller |
| 3,875,300 | A | 4/1975 | Homm et al. |
| 3,929,678 | A | 12/1975 | Laughlin |
| 3,957,921 | A | 5/1976 | Iwahashi et al. |
| 3,967,921 | A | 7/1976 | Haberli et al. |
| 4,020,156 | A | 4/1977 | Murray et al. |
| 4,024,078 | A | 5/1977 | Gilbert et al. |
| 4,051,081 | A | 9/1977 | Jabs et al. |
| 4,089,945 | A | 5/1978 | Brinkman et al. |
| 4,149,551 | A | 4/1979 | Benjamin et al. |
| 4,185,125 | A | 1/1980 | Kimura et al. |
| 4,196,190 | A | 4/1980 | Gehman et al. |
| 4,197,865 | A | 4/1980 | Jacquet et al. |
| 4,206,196 | A | 6/1980 | Davis |
| 4,217,914 | A | 8/1980 | Jacquet et al. |
| 4,272,511 | A | 6/1981 | Papantoniou et al. |
| 4,286,016 | A | 8/1981 | Dimond |
| 4,315,965 | A | 2/1982 | Mason |
| 4,323,525 | A | 4/1982 | Bornat |
| 4,323,683 | A | 4/1982 | Bolich, Jr. et al. |
| 4,340,583 | A | 7/1982 | Wason |
| 4,342,813 | A | 8/1982 | Erickson |
| 4,345,080 | A | 8/1982 | Bolich, Jr. |
| D266,829 | S | 11/1982 | Yoshizawa et al. |
| 4,377,615 | A | 3/1983 | Suzuki |
| 4,379,753 | A | 4/1983 | Bolich, Jr. |
| 4,381,919 | A | 5/1983 | Jacquet et al. |
| 4,415,617 | A | 11/1983 | D |
| 4,422,853 | A | 12/1983 | Jacquet et al. |
| 4,448,699 | A | 5/1984 | Barrat et al. |
| 4,470,982 | A | 9/1984 | Winkler |
| 4,507,280 | A | 3/1985 | Pohl et al. |
| 4,529,586 | A | 7/1985 | De et al. |
| 4,536,361 | A | 8/1985 | Torobin |
| 4,565,647 | A | 1/1986 | Llenado |
| D286,450 | S | 10/1986 | Tovey |
| 4,635,351 | A | 1/1987 | Koch et al. |
| 4,639,390 | A | 1/1987 | Shoji |
| 4,663,158 | A | 5/1987 | Wolfram et al. |
| 4,710,374 | A | 12/1987 | Grollier et al. |
| 4,723,362 | A | 2/1988 | Boerger |
| 4,727,410 | A | 2/1988 | Higgins, III |
| 4,822,613 | A | 4/1989 | Rodero |
| 4,885,107 | A | 12/1989 | Wetzel |
| 4,892,758 | A | 1/1990 | Serbiak |
| 4,976,953 | A | 12/1990 | Orr et al. |
| 4,990,280 | A | 2/1991 | Thorengaard |
| 5,034,421 | A | 7/1991 | Fuisz |
| 5,052,296 | A | 10/1991 | Shiba |
| 5,055,384 | A | 10/1991 | Kuehnert |
| 5,061,481 | A | 10/1991 | Suzuki et al. |
| 5,062,889 | A | 11/1991 | Hoehl et al. |
| 5,062,994 | A | 11/1991 | Imperatori |
| 5,094,853 | A | 3/1992 | Hagarty |
| 5,098,636 | A | 3/1992 | Balk |
| 5,100,657 | A | 3/1992 | Ansher-jackson et al. |
| 5,100,658 | A | 3/1992 | Bolich, Jr. et al. |
| 5,102,129 | A | 4/1992 | Roberts |
| 5,104,646 | A | 4/1992 | Bolich, Jr. |
| 5,106,609 | A | 4/1992 | Bolich, Jr. |
| 5,112,515 | A | 5/1992 | Buxton et al. |
| 5,166,276 | A | 11/1992 | Hayama et al. |
| D334,420 | S | 3/1993 | Copeland et al. |
| 5,220,033 | A | 6/1993 | Kamei et al. |
| 5,230,853 | A | 7/1993 | Colegrove |
| 5,261,426 | A | 11/1993 | Kellett et al. |
| 5,280,079 | A | 1/1994 | Allen et al. |
| RE34,584 | E | 4/1994 | Grote et al. |
| D351,345 | S | 10/1994 | Geho |
| 5,364,627 | A | 11/1994 | Song |
| 5,391,368 | A | 2/1995 | Gerstein |
| D357,115 | S | 4/1995 | Ashley et al. |
| 5,409,703 | A | 4/1995 | Mcanalley et al. |
| D358,025 | S | 5/1995 | Martin et al. |
| 5,415,810 | A | 5/1995 | Lee |
| 5,429,628 | A | 7/1995 | Trinh et al. |
| 5,444,113 | A | 8/1995 | Sinclair et al. |
| 5,446,079 | A | 8/1995 | Buchanan et al. |
| 5,455,114 | A | 10/1995 | Ohmory |
| 5,457,895 | A | 10/1995 | Thompson et al. |
| 5,458,433 | A | 10/1995 | Stastny |
| 5,470,424 | A | 11/1995 | Isaac |
| 5,470,492 | A | 11/1995 | Childs et al. |
| 5,476,597 | A | 12/1995 | Sakata et al. |
| 5,501,238 | A | 3/1996 | Borstel et al. |
| 5,533,636 | A | 7/1996 | Reiker |
| 5,538,735 | A | 7/1996 | Ahn |
| 5,580,481 | A | 12/1996 | Sakata et al. |
| 5,582,786 | A | 12/1996 | Brunskill et al. |
| D378,180 | S | 2/1997 | Hayes |
| 5,660,845 | A | 8/1997 | Trinh et al. |
| 5,672,576 | A | 9/1997 | Behrens et al. |
| 5,673,576 | A | 10/1997 | Chen et al. |
| 5,674,478 | A | 10/1997 | Dodd |
| 5,716,692 | A | 2/1998 | Warner |
| 5,750,122 | A | 5/1998 | Evans |
| 5,756,438 | A | 5/1998 | Rau et al. |
| 5,780,047 | A | 7/1998 | Kamiya et al. |
| 5,780,418 | A | 7/1998 | Niinaka |
| D398,847 | S | 9/1998 | Wyslotsky |

(56) References Cited

U.S. PATENT DOCUMENTS

| | | |
|---|---|---|
| D399,260 S | 10/1998 | Thimote |
| 5,840,675 A | 11/1998 | Yeazell |
| 5,849,378 A | 12/1998 | Gask |
| 5,879,493 A | 3/1999 | Johnson |
| D407,640 S | 4/1999 | Crapser et al. |
| D408,223 S | 4/1999 | Henry |
| 5,911,224 A | 6/1999 | Berger |
| 5,925,603 A | 7/1999 | D |
| 5,952,286 A | 9/1999 | Puvvada et al. |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,028,016 A | 2/2000 | Yahiaoui et al. |
| 6,029,808 A | 2/2000 | Peck et al. |
| 6,034,043 A | 3/2000 | Fujiwara |
| 6,074,997 A | 6/2000 | Rau et al. |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,319,510 B1 | 11/2001 | Yates |
| 6,335,312 B1 | 1/2002 | Coffindaffer et al. |
| 6,365,142 B1 | 4/2002 | Tamura |
| 6,382,526 B1 | 5/2002 | Reneker et al. |
| 6,420,625 B1 | 7/2002 | Jones |
| 6,440,926 B1 | 8/2002 | Spadoni et al. |
| D462,900 S | 9/2002 | Yamada et al. |
| 6,448,462 B2 | 9/2002 | Groitzsch |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| 6,552,123 B1 | 4/2003 | Katayama |
| D479,561 S | 9/2003 | Meyer |
| 6,623,694 B1 | 9/2003 | Ferguson et al. |
| D484,749 S | 1/2004 | Garraway |
| 6,723,160 B2 | 4/2004 | Mackey et al. |
| D489,162 S | 5/2004 | Dings-plooij |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,898,819 B2 | 5/2005 | Tanaka et al. |
| D509,935 S | 9/2005 | Burt |
| 6,943,200 B1 | 9/2005 | Corrand et al. |
| 6,946,506 B2 | 9/2005 | Bond |
| D515,915 S | 2/2006 | Karim |
| 7,015,181 B2 | 3/2006 | Lambino |
| 7,041,369 B1 | 5/2006 | Mackey et al. |
| 7,115,551 B2 | 10/2006 | Hasenoehrl |
| 7,169,740 B2 | 1/2007 | Sommerville-roberts |
| RE39,557 E | 4/2007 | Moe |
| 7,208,460 B2 | 4/2007 | Shefer et al. |
| 7,221,900 B2 | 5/2007 | Reade et al. |
| D549,051 S | 8/2007 | Nordwall |
| 7,285,520 B2 | 10/2007 | Krzysik |
| 7,291,300 B2 | 11/2007 | Chhabra et al. |
| 7,387,787 B2 | 6/2008 | Fox |
| D576,753 S | 9/2008 | Mukai |
| D577,332 S | 9/2008 | Moore |
| 7,429,273 B2 | 9/2008 | De |
| D578,881 S | 10/2008 | Friedland |
| D588,332 S | 3/2009 | Phelan |
| 7,507,698 B2 | 3/2009 | Franzolin |
| 7,704,328 B2 | 4/2010 | Bailey et al. |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D644,541 S | 9/2011 | Schrader et al. |
| 8,049,061 B2 | 11/2011 | Ehrenreich et al. |
| D651,096 S | 12/2011 | Nakagiri |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,232 B2 | 1/2013 | Pourdeyhimi |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,453,653 B2 | 6/2013 | Mishra et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| 8,785,361 B2 | 7/2014 | Sivik |
| D712,159 S | 9/2014 | Clerici et al. |
| D712,822 S | 9/2014 | Brusaw et al. |
| 8,962,501 B2 | 2/2015 | Johnson et al. |
| 8,980,816 B2 | 3/2015 | Dreher |
| 9,005,635 B2 | 4/2015 | Darcy et al. |
| 9,062,186 B2 | 6/2015 | Longdon et al. |
| D739,227 S | 9/2015 | Mitchell et al. |
| 9,125,811 B2 | 9/2015 | Tojo et al. |
| D740,928 S | 10/2015 | Bruining et al. |
| 9,163,205 B2 | 10/2015 | Sivik et al. |
| 9,173,826 B2 | 11/2015 | Schwartz et al. |
| 9,175,250 B2 | 11/2015 | Sivik et al. |
| 9,198,838 B2 | 12/2015 | Glenn, Jr. |
| D748,240 S | 1/2016 | Goode |
| 9,421,153 B2 | 8/2016 | Sivik et al. |
| D769,522 S | 10/2016 | Venet |
| D771,788 S | 11/2016 | Duckwitz |
| 9,480,628 B2 | 11/2016 | Sivik et al. |
| D774,086 S | 12/2016 | Montes et al. |
| D775,198 S | 12/2016 | Montes et al. |
| 9,539,444 B2 | 1/2017 | Kinoshita et al. |
| 9,545,364 B2 | 1/2017 | Glenn, Jr. et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| 9,902,077 B2 | 2/2018 | Park et al. |
| D811,922 S | 3/2018 | Lefave |
| D811,935 S | 3/2018 | Hughes |
| D819,836 S | 6/2018 | Noël |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |

(56) References Cited

U.S. PATENT DOCUMENTS

| | | |
|---|---|---|
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,646,413 B2 | 5/2020 | Sivik et al. |
| 10,694,917 B2 | 6/2020 | Dreher et al. |
| D901,115 S | 11/2020 | Carlson et al. |
| D903,152 S | 11/2020 | Chao |
| 10,821,056 B2 | 11/2020 | Swartz et al. |
| D906,802 S | 1/2021 | Chi |
| 10,894,005 B2 | 1/2021 | Sivik et al. |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 11,351,094 B2 * | 6/2022 | Hamersky ............... A61Q 5/12 |
| 11,395,789 B2 | 7/2022 | Pratt et al. |
| 11,419,808 B2 * | 8/2022 | Hilvert ............... A61K 8/8176 |
| 11,679,066 B2 | 6/2023 | Song et al. |
| 2001/0037851 A1 | 11/2001 | Mortellite |
| 2002/0044968 A1 | 4/2002 | Van |
| 2002/0064510 A1 | 5/2002 | Dalrymple et al. |
| 2002/0077264 A1 | 6/2002 | Roberts et al. |
| 2002/0081732 A1 | 6/2002 | Bowlin et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0161088 A1 | 10/2002 | Kochvar |
| 2002/0173213 A1 | 11/2002 | Chu |
| 2002/0175449 A1 | 11/2002 | Chu et al. |
| 2002/0176827 A1 | 11/2002 | Rajaiah |
| 2002/0177621 A1 | 11/2002 | Hanada et al. |
| 2002/0187181 A1 | 12/2002 | Godbey et al. |
| 2003/0013369 A1 | 1/2003 | Soane et al. |
| 2003/0017208 A1 | 1/2003 | Ignatious |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0054966 A1 | 3/2003 | Bone et al. |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0114332 A1 | 6/2003 | Ramcharan et al. |
| 2003/0141662 A1 | 7/2003 | Kost et al. |
| 2003/0166489 A1 | 9/2003 | Van et al. |
| 2003/0166495 A1 | 9/2003 | Wang |
| 2003/0180242 A1 | 9/2003 | Eccard et al. |
| 2003/0185872 A1 | 10/2003 | Kochinke |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0224959 A1 | 12/2003 | Smith |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Rachse et al. |
| 2004/0059055 A1 | 3/2004 | Inada |
| 2004/0071742 A1 | 4/2004 | Popplewell |
| 2004/0071755 A1 | 4/2004 | Fox |
| 2004/0082239 A1 | 4/2004 | Di et al. |
| 2004/0108615 A1 | 6/2004 | Foley |
| 2004/0110656 A1 | 6/2004 | Casey et al. |
| 2004/0116018 A1 | 6/2004 | Fenwick et al. |
| 2004/0116539 A1 | 6/2004 | Biercevicz et al. |
| 2004/0118852 A1 | 6/2004 | Barmore et al. |
| 2004/0126585 A1 | 7/2004 | Kerins et al. |
| 2004/0170836 A1 | 9/2004 | Bond |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2004/0253434 A1 | 12/2004 | Patel |
| 2004/0266300 A1 | 12/2004 | Isele et al. |
| 2005/0003048 A1 | 1/2005 | Pearce |
| 2005/0003991 A1 | 1/2005 | Macquarrie |
| 2005/0008776 A1 | 1/2005 | Chhabra |
| 2005/0069575 A1 | 3/2005 | Fox |
| 2005/0118237 A1 | 6/2005 | Krzysik et al. |
| 2005/0136772 A1 | 6/2005 | Chen et al. |
| 2005/0136780 A1 | 6/2005 | Clark et al. |
| 2005/0137115 A1 | 6/2005 | Cole et al. |
| 2005/0137272 A1 | 6/2005 | Gaserod |
| 2005/0159730 A1 | 7/2005 | Kathrani et al. |
| 2005/0180962 A1 | 8/2005 | Raz et al. |
| 2005/0202992 A1 | 9/2005 | Grandio et al. |
| 2005/0209574 A1 | 9/2005 | Boehringer |
| 2005/0220745 A1 | 10/2005 | Lu |
| 2005/0232954 A1 | 10/2005 | Yoshinari et al. |
| 2005/0267005 A1 | 12/2005 | Dasque et al. |
| 2005/0272836 A1 | 12/2005 | Yaginuma et al. |
| 2005/0281757 A1 | 12/2005 | Ibrahim |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0083784 A1 | 4/2006 | Ignatious |
| 2006/0128592 A1 | 6/2006 | Ross |
| 2006/0134412 A1 | 6/2006 | Mackey |
| 2006/0159730 A1 | 7/2006 | Simon |
| 2006/0160453 A1 | 7/2006 | Suh |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0054579 A1 | 3/2007 | Baker, Jr. |
| 2007/0098749 A1 | 5/2007 | Eknoian et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0269651 A1 | 11/2007 | Denome et al. |
| 2007/0298064 A1 | 12/2007 | Koslow |
| 2008/0008906 A1 | 1/2008 | Catalfamo |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0149119 A1 | 6/2008 | Shen |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0269095 A1 | 10/2008 | Aubrun-sonneville |
| 2008/0276178 A1 | 11/2008 | Fadell et al. |
| 2008/0279905 A1 | 11/2008 | Kawamoto et al. |
| 2008/0292669 A1 | 11/2008 | Deng et al. |
| 2008/0293839 A1 | 11/2008 | Stobby |
| 2009/0004254 A1 | 1/2009 | Maibach |
| 2009/0041820 A1 | 2/2009 | Wu et al. |
| 2009/0054860 A1 | 2/2009 | Young et al. |
| 2009/0061225 A1 | 3/2009 | Bailey et al. |
| 2009/0061496 A1 | 3/2009 | Kuhn |
| 2009/0061719 A1 | 3/2009 | Shibutani |
| 2009/0144913 A1 | 6/2009 | Yu et al. |
| 2009/0155326 A1 | 6/2009 | Mack |
| 2009/0155383 A1 | 6/2009 | Kitko et al. |
| 2009/0181587 A1 | 7/2009 | Kang |

(56) References Cited

U.S. PATENT DOCUMENTS

| | | |
|---|---|---|
| 2009/0197787 A1 | 8/2009 | Venet et al. |
| 2009/0232873 A1 | 9/2009 | Glenn, Jr. et al. |
| 2009/0249558 A1 | 10/2009 | Fileccia |
| 2009/0258099 A1 | 10/2009 | Brown et al. |
| 2009/0263342 A1 | 10/2009 | Glenn, Jr. et al. |
| 2009/0285718 A1 | 11/2009 | Privitera |
| 2009/0291282 A1 | 11/2009 | Kitamura et al. |
| 2009/0293281 A1 | 12/2009 | Bruno |
| 2010/0018641 A1 | 1/2010 | Branham |
| 2010/0021517 A1 | 1/2010 | Ahlers |
| 2010/0098745 A1 | 4/2010 | Staab |
| 2010/0105821 A1 | 4/2010 | Verrall |
| 2010/0135921 A1 | 6/2010 | Hughes et al. |
| 2010/0150976 A1 | 6/2010 | Schnitzler |
| 2010/0166854 A1 | 7/2010 | Michniak-kohn |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0291165 A1 | 11/2010 | Glenn, Jr. et al. |
| 2010/0298188 A1 | 11/2010 | Glenn, Jr. et al. |
| 2011/0014252 A1 | 1/2011 | Sagel et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0045041 A1 | 2/2011 | Golubovic-Liakopoulos et al. |
| 2011/0123596 A1 | 5/2011 | Baecker et al. |
| 2011/0129510 A1 | 6/2011 | Liebmann |
| 2011/0136719 A1 | 6/2011 | Jalbert |
| 2011/0159267 A1 | 6/2011 | Lee |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1 | 8/2011 | Glenn, Jr. et al. |
| 2011/0223381 A1 | 9/2011 | Sauter |
| 2011/0230112 A1 | 9/2011 | Rose |
| 2011/0250256 A1 | 10/2011 | Hyun-oh et al. |
| 2011/0287687 A1 | 11/2011 | Kramer et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0048769 A1 | 3/2012 | Sivik |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053108 A1 | 3/2012 | Glenn, Jr. |
| 2012/0058100 A1 | 3/2012 | Shastri et al. |
| 2012/0058166 A1 | 3/2012 | Glenn, Jr. |
| 2012/0082037 A1 | 4/2012 | Wang |
| 2012/0107534 A1 | 5/2012 | Wnuk et al. |
| 2012/0172831 A1 | 7/2012 | Darcy |
| 2012/0215148 A1 | 8/2012 | Ewert |
| 2012/0237576 A1 | 9/2012 | Gordon |
| 2012/0258902 A1 | 10/2012 | Parrish et al. |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0052277 A1 | 2/2013 | Weiss et al. |
| 2013/0142852 A1 | 6/2013 | Tojo et al. |
| 2013/0171421 A1 | 7/2013 | Weisman |
| 2013/0230482 A1 | 9/2013 | Saguchi et al. |
| 2013/0236520 A1 | 9/2013 | Popovsky et al. |
| 2013/0280979 A1 | 10/2013 | Mckee |
| 2013/0303419 A1 | 11/2013 | Glenn, Jr. et al. |
| 2014/0017402 A1 | 1/2014 | Kleinwaechter et al. |
| 2014/0039114 A1 | 2/2014 | Hagihara et al. |
| 2014/0105946 A1 | 4/2014 | Glenn, Jr. et al. |
| 2014/0127145 A1 | 5/2014 | Deckner |
| 2014/0128345 A1 | 5/2014 | Woodrow et al. |
| 2014/0265007 A1 | 9/2014 | Bruning et al. |
| 2014/0271744 A1 | 9/2014 | Glenn, Jr. et al. |
| 2014/0271745 A1 | 9/2014 | Glenn, Jr. et al. |
| 2014/0329428 A1 | 11/2014 | Glenn, Jr. |
| 2015/0044157 A1 | 2/2015 | Kulkarni et al. |
| 2015/0071572 A1 | 3/2015 | Dreher |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0250109 A1 | 9/2016 | Dreher et al. |
| 2016/0324741 A1 | 11/2016 | Baig |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0015643 A1 | 1/2018 | Patel et al. |
| 2018/0104177 A1 | 4/2018 | Constantine et al. |
| 2018/0110710 A1 | 4/2018 | Zhao et al. |
| 2018/0140469 A1 | 5/2018 | Kane et al. |
| 2018/0163325 A1 | 6/2018 | Glenn, Jr. et al. |
| 2018/0258555 A1 | 9/2018 | Glenn, Jr. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0105243 A1 | 4/2019 | Song et al. |
| 2019/0282457 A1 | 9/2019 | Pratt |
| 2019/0282461 A1 | 9/2019 | Glassmeyer |
| 2019/0350819 A1 | 11/2019 | Hamersky |
| 2020/0071851 A1 | 3/2020 | Glenn, Jr. et al. |
| 2020/0093710 A1 | 3/2020 | Hamersky |
| 2020/0214946 A1 | 7/2020 | Chan et al. |
| 2020/0261326 A1 | 8/2020 | Sivik et al. |
| 2020/0275818 A1 | 9/2020 | Gamble |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0121373 A1 | 4/2021 | Tan et al. |
| 2021/0128417 A1 | 5/2021 | Sivik et al. |
| 2021/0137798 A1 | 5/2021 | Sivik et al. |
| 2021/0147763 A1 | 5/2021 | Tan et al. |
| 2021/0189602 A1 | 6/2021 | Glenn, Jr. et al. |
| 2021/0322290 A1 | 10/2021 | Lynch et al. |
| 2021/0401677 A1 | 12/2021 | Song |
| 2022/0054365 A1 | 2/2022 | Xu et al. |
| 2022/0323309 A1 | 10/2022 | Pratt et al. |
| 2023/0190588 A1 | 6/2023 | Song |

FOREIGN PATENT DOCUMENTS

| | | |
|---|---|---|
| CA | 2524099 A1 | 4/2006 |
| CA | 2695068 A1 | 9/2010 |
| CA | 166297 | 5/2018 |
| CA | 169627 S | 5/2018 |
| CN | 1138091 | 12/1996 |
| CN | 1219388 | 6/1999 |
| CN | 1268558 | 10/2000 |
| CN | 1357613 A | 7/2002 |
| CN | 1454231 A | 11/2003 |
| CN | 1473194 A | 2/2004 |
| CN | 1530431 A | 9/2004 |
| CN | 1583991 A | 2/2005 |
| CN | 1726074 A | 1/2006 |
| CN | 3648760 | 5/2007 |
| CN | 101161877 A | 4/2008 |

(56) References Cited

FOREIGN PATENT DOCUMENTS

| | | | |
|---|---|---|---|
| CN | 101424009 A | 5/2009 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 106916659 A | 7/2017 |
| CN | 304537587 | 3/2018 |
| CN | 109589279 B | 3/2020 |
| DE | 19607851 A1 | 9/1997 |
| DE | 10331767 A1 | 2/2005 |
| DE | 100932 | 4/2018 |
| DE | 100938 | 4/2018 |
| DE | 101063 | 5/2018 |
| DE | 101100 | 5/2018 |
| DE | 101101 | 5/2018 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1214879 A2 | 6/2002 |
| EP | 1227152 A1 | 7/2002 |
| EP | 1217987 B1 | 12/2004 |
| EP | 1574561 A1 | 9/2005 |
| EP | 1160311 B1 | 3/2006 |
| EP | 1887036 A2 | 2/2008 |
| EP | 1958532 A2 | 8/2008 |
| EP | 2085434 A1 | 8/2009 |
| EP | 1317916 B1 | 10/2010 |
| EP | 2246031 A1 | 11/2010 |
| FR | 2871685 A1 | 12/2005 |
| FR | 2886845 A1 | 12/2006 |
| GB | 2107579 A | 5/1983 |
| GB | 2235204 A | 2/1991 |
| GB | 2355008 A | 4/2001 |
| GB | 2378407 A | 2/2003 |
| IN | 20150354411 | 5/2017 |
| JP | S4912158 A | 2/1974 |
| JP | 58021608 | 2/1983 |
| JP | S58216109 A | 12/1983 |
| JP | S59163458 A | 9/1984 |
| JP | S6272609 A | 4/1987 |
| JP | S6272610 A | 4/1987 |
| JP | S6281432 A | 4/1987 |
| JP | S6281462 A | 4/1987 |
| JP | S6346251 A | 2/1988 |
| JP | S63156715 A | 6/1988 |
| JP | H01172319 A | 7/1989 |
| JP | H01229805 A | 9/1989 |
| JP | H01313418 A | 12/1989 |
| JP | H0275650 A | 3/1990 |
| JP | H05344873 A | 12/1993 |
| JP | H0617083 A | 1/1994 |
| JP | 0753349 | 2/1995 |
| JP | H0789852 A | 4/1995 |
| JP | H07173724 A | 7/1995 |
| JP | H08325133 A | 12/1996 |
| JP | H09216909 A | 8/1997 |
| JP | 10158700 A | 6/1998 |
| JP | H10251371 A | 9/1998 |
| JP | H10251952 A | 9/1998 |
| JP | H11513053 A | 11/1999 |
| JP | 2000053998 A | 2/2000 |
| JP | 2000169896 A | 6/2000 |
| JP | 2000212828 A | 8/2000 |
| JP | 2000229841 A | 8/2000 |
| JP | 2001302868 A | 10/2001 |
| JP | 2001519376 A | 10/2001 |
| JP | 2001520983 A | 11/2001 |
| JP | 2002201531 A | 7/2002 |
| JP | 2002226895 A | 8/2002 |
| JP | 2003073700 A | 3/2003 |
| JP | 2003082397 A | 3/2003 |
| JP | 2004509198 A | 3/2004 |
| JP | 2004256799 A | 9/2004 |
| JP | 2004533551 A | 11/2004 |
| JP | 2004345983 A | 12/2004 |
| JP | 2005171063 A | 6/2005 |
| JP | 2005538202 A | 12/2005 |
| JP | 2006002337 A | 1/2006 |
| JP | 2006056835 A | 3/2006 |
| JP | 3828217 B2 | 7/2006 |
| JP | 2007001889 A | 1/2007 |
| JP | 2007091954 A | 4/2007 |
| JP | 2007197365 A | 8/2007 |
| JP | 2007197540 A | 8/2007 |
| JP | 2007528748 A | 10/2007 |
| JP | 4128580 B2 | 5/2008 |
| JP | 2008156807 A | 7/2008 |
| JP | 2008525436 A | 7/2008 |
| JP | 2009079329 A | 4/2009 |
| JP | 2009533569 A | 9/2009 |
| JP | 4510221 B2 | 5/2010 |
| JP | 2010100966 A | 5/2010 |
| JP | 2010126856 A | 6/2010 |
| JP | 2013505375 A | 2/2013 |
| JP | 2013099467 A | 5/2013 |
| JP | 5344873 B2 | 8/2013 |
| JP | 2013531145 A | 8/2013 |
| JP | 2013531748 A | 8/2013 |
| JP | 2015509147 A | 3/2015 |
| JP | 5821609 B2 | 10/2015 |
| JP | 6272610 B2 | 1/2018 |
| KR | 20020003442 A | 1/2002 |
| KR | 20040094520 A | 11/2004 |
| TW | 232027 B | 10/1994 |
| WO | 8301943 A1 | 6/1983 |
| WO | 9514495 A1 | 6/1995 |
| WO | 9918182 A1 | 4/1999 |
| WO | 9951715 A1 | 10/1999 |
| WO | 9957155 A1 | 11/1999 |
| WO | 0042992 A2 | 7/2000 |
| WO | 0107194 A1 | 2/2001 |
| WO | 0119948 A1 | 3/2001 |
| WO | 0125322 A1 | 4/2001 |
| WO | 0125393 A1 | 4/2001 |
| WO | 200125322 A1 | 4/2001 |
| WO | 2001024770 A1 | 4/2001 |
| WO | 200154667 A1 | 8/2001 |
| WO | 2001054667 A1 | 8/2001 |
| WO | 0183657 A2 | 11/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2006106514 A2 | 10/2006 |
| WO | 2006130647 A1 | 12/2006 |
| WO | 2007022229 A1 | 2/2007 |
| WO | 2007033598 A1 | 3/2007 |
| WO | 2007093558 A1 | 8/2007 |
| WO | 2007093619 A1 | 8/2007 |
| WO | 2007102119 A1 | 9/2007 |
| WO | 2008015641 A2 | 2/2008 |
| WO | 2008049242 A1 | 5/2008 |
| WO | 2008104954 A2 | 9/2008 |
| WO | 2009019571 A2 | 2/2009 |
| WO | 2009095891 A1 | 8/2009 |
| WO | 2010006708 A1 | 1/2010 |
| WO | 2010077627 A2 | 7/2010 |
| WO | 2010085569 A1 | 7/2010 |
| WO | 2012120199 A1 | 9/2012 |
| WO | 2014158472 A1 | 10/2014 |
| WO | 2015034975 A1 | 3/2015 |
| WO | 2015153185 A1 | 10/2015 |

(56) References Cited

FOREIGN PATENT DOCUMENTS

| | | |
|---|---|---|
| WO | 2019001940 A1 | 1/2019 |
| WO | 2020192519 A1 | 10/2020 |

OTHER PUBLICATIONS

All Office Actions; U.S. Appl. No. 13/173,639, filed Jun. 30, 2011.
All Office Actions; U.S. Appl. No. 13/229,825, filed Sep. 12, 2011.
All Office Actions; U.S. Appl. No. 14/334,862, filed Jul. 18, 2014.
All Office Actions; U.S. Appl. No. 15/170,125, filed Jun. 1, 2016.
All Office Actions; U.S. Appl. No. 15/374,486, filed Dec. 9, 2016.
All Office Actions; U.S. Appl. No. 15/978,503, filed May 14, 2018.
All Office Actions; U.S. Appl. No. 16/674,837, filed Nov. 5, 2019.
All Office Actions; U.S. Appl. No. 17/184,712, filed Feb. 25, 2021.
Ashland, Klucel hydroxypropylcelllose, accessed at http://www.ashland.com/Ashland/Static/Documents/ASI/PC_11229_Klucel_HPC.pdf on Apr. 20, 2016.
Francis Ignatious, Linghong Sun, Chao-Pin Lee, and John Baldoni. Electrospun Nanofibers in Oral Drug Delivery—ExpertReview. Pharmaceutical Research, vol. 27, No. 4, Apr. 2010, pp. 576-588. Published online Feb. 9, 2010.
Gemz Hair Care. Perfect Pairs. Publication date unavailable. Visited Jan. 26, 2022. https://shopgemz.com/collections/perfect-pairs (Year: 0).
Makadia, et al., "Poly Lactic-co-Glycolic Acid (PLGA) as Biodegradable ControlledDrug Delivery Carrier", Polymers, 3, pp. 1377-1397 (2011).
Menard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.
Minifibers, Inc., accessed on line at http://www.minifibers.com/documents/Choosing-the-Proper-Short-Cut-Fiber.pdf Oct. 3, 2016.
Overview of pharmaceutical excipients used in tablets and capsules in Drug Topics, dated Oct. 24, 2008. Downloaded Sep. 20, 2016 from http://drugtopics.modernmedicine.com/drugtopics/news/modernmedicine/ modernmedicinenews/overviewpharmaceuticalexcipientsusedtablets.
Smith, et al., "Nanofibrous Scaffolds and Their Biological Effects", Nanotechnologiesfor the Life Sciences, vol. 9, pp. 188-215 (2006).
W S Ratnayake and D S Jackson. Gelatinization and solubility of corn starch during heating in excess water. Faculty u Publications in Food Science and Technology, Jan. 1, 2006. Also published in Journal of Agricultural and Food Chemistry 54:1 O(2006), pp. 3712-3716.
Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue No. 2-3, Nov. 1, 2007, p. 79-87.
"Green Chemistry", Huazhong University of Science and Technology Press, published on Jun. 30, 2008, pp. 6.
Adhesives Research (Pennsylvania, http://12.4.33.51/news/apresmed.htm).
All final and non-final office actions for U.S. Appl. No. 29/728,688 (P&G Case D-02862).
All Office Actions; U.S. Appl. No. 14/690,593, filed Apr. 20, 2015.
All Office Actions; U.S. Appl. No. 15/665,886, filed Aug. 1, 2017.
All Office Actions; U.S. Appl. No. 15/979,961, filed May 15, 2018.
All Office Actions; U.S. Appl. No. 15/981,096, filed May 16, 2018.
All Office Actions; U.S. Appl. No. 16/431,028, filed Jun. 4, 2019.
All Office Actions; U.S. Appl. No. 16/431,115, filed Jun. 4, 2019.
All Office Actions; U.S. Appl. No. 16/577,120, filed Sep. 20, 2019.
All Office Actions; U.S. Appl. No. 16/589,504, filed Oct. 1, 2019.
All Office Actions; U.S. Appl. No. 16/901,548, filed Jun. 15, 2020.
All Office Actions; U.S. Appl. No. 16/912,876, filed Jun. 26, 2020.
All Office Actions; U.S. Appl. No. 16/918,292, filed Jul. 1, 2020.
All Office Actions; U.S. Appl. No. 16/953,975, filed Nov. 20, 2020.
All Office Actions; U.S. Appl. No. 17/070,205, filed Oct. 14, 2020.
All Office Actions; U.S. Appl. No. 17/357,119, filed Jun. 24, 2021.
All Office Actions; U.S. Appl. No. 29/672,822, filed Dec. 10, 2018.
All Office Actions; U.S. Appl. No. 29/676,338, filed Jan. 10, 2019.
All Office Actions; U.S. Appl. No. 29/707,807, filed Oct. 1, 2019.
All Office Actions; U.S. Appl. No. 29/707,809, filed Oct. 1, 2019.
All Office Actions; U.S. Appl. No. 29/728,687, filed Mar. 20, 2020.
All Office Actions; U.S. Appl. No. 29/766,885, filed Jan. 19, 2021.
All Office Actions; U.S. Appl. No. 29/815,500, filed Nov. 15, 2021.
All Office Actions; U.S. Appl. No. 29/819,499, filed Dec. 15, 2021.
Amerilab Technologies, Inc. (Minnesota, http://www.amerilabtech.comm/).
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009, year 2009, 1 pg.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDalNuo9_cQSOpPwCmsmmdGA1YOUSekQEaAh0iEALw_wcB (Year: 2021).
Definition of Derivative by Merriam Webster Online Dictionary, Year, 2021.
Design of "Detergent tablets" (Design Registration No. 000634142-0003), (No. of Publicly known information: HH18274488), Registered Community Designs Bulletin, published by EUIPO on Jan. 9, 2007, 4 pgs.
Design of "Detergent tablets" (Design Registration No. 000634142-0004), (No. of Publicly known information: HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Dissolving Soap Strips (Ranir LLC, Michigan, www.ranir.com).
Dow, UCARE™ Polymer LR-400, Technical Data Sheet, Downloaded in Mar. 2022, 4 pages.
Encyclopedia of Polymer Science and Engineering, vol. 15, 2nd ed., p. 204 308 Silicones, year 1989.
Final Office Action; U.S. Appl. No. 14/690,593 dated Aug. 17, 2017.
Final Office Action; U.S. Appl. No. 14/690,593 dated Jul. 21, 2016.
Final Office Action; U.S. Appl. No. 15/665,886 dated Dec. 28, 2107.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet : http://candle-box.com/product/%EC%9C%A1%EA%B0%81-4%EA%B5%AC-%EB%B9%84%EB%88%84%EB%AA%B0 %EB%93%9C/2206/?page_4=3#none, dated Sep. 10, 2019, 16 pgs.
Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Japanese Paper Soap (http://www.wishingfish.com/papersoap.html).
Karen Duis et al, "Environmental fate and effects of water-soluble synthetic organic polymers used in cosmetic products", Environmental Sciences Europe, vol. 33, Article No. 21, Feb. 16, 2021, 78 pages.
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].
Le Laboratoire du Bain (France, http://www.laboudubain.com/).

(56) References Cited

OTHER PUBLICATIONS

M.K. Industries (Gujarat India, http://www.soapstrips.com).
Megulars Car Wash Strips: Megulars Inc. California, http://www.automotivedigesl.com/view_art.asp?articles!D=12414.
Michelle Villett, Why You Need a Sulfate-Free Shampoo, The Skincare Edit, updated date: Jan. 25, 2019, Original publication date: Feb. 22, 2016 (Year: 2016), 7 pages. Mar. 23, 2021.
MOVA Pharmaceutical and Kosmos (USA, http:/lwww.icon-pr.com/news/news/prinl.cfm?inv_id=256-1).
Ni Genshan et al. "Drug Classification and Pharmacology Summary", PLA Press, published on Apr. 30, 1988, pp. 3.
Non-Final Office Action; U.S. Appl. No. 17/070,205 dated Nov. 23, 2021.
Non-Final Office Action; U.S. Appl. No. 16/901,548 dated Aug. 3, 2021.
Non Final Office Action; U.S. Appl. No. 14/690,593 dated Mar. 1, 2016.
Non Final Office Action; U.S. Appl. No. 14/690,593 dated Nov. 22, 2016.
Non Final Office Action; U.S. Appl. No. 15/665,886 dated Sep. 1, 2107.
Notice of Allowance; U.S. Appl. No. 15/665,886 dated Jun. 10, 2020.
Notice of Allowance; U.S. Appl. No. 16/901,548 dated Jan. 6, 2022.
Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).
PCT International Search Report and Written Opinion for PCT/US2018/030762 dated Aug. 7, 2018.
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.
Pure Soap Leafz: (Soap UNLTD. Netherlands, http://www.upandunder.com.uk/eshop/catalogue/testbs.asp?Manufacturer_ID=252&Activity_ID=33&Description_ID=157).
Raymond C Rowe et al., Polyvinyl Alcohol, Handbook of Pharmaceutical Excipients, 2009, Sixth Edition, Pharmaceutical Press, 564-565.
Retrieved from: https ://www.craftcuts.com/hexagon-craft-shape.html Hexagon wood cutouts, www.craftcuts.com, 1 page, reviewed as early as May 2018 (Year: 2018), 16 pgs.
Rounded hexagon shape, announced 2016 [online], [site visited Oct. 20, 2021], Available from internet, URL:https://www.vexels.com/png-svg/preview/139199/rounded-hexagon-shape (Year: 2016).
Sahin et al. "A Study on Physical and Chemical Properties of Cellulose Paper Immersed in Various Solvent Mixtures" International Journal Of Molecular Sciences, Jan. 2008; 9(1): 78-88.
Sanipro Sanitary Products (Italy, http://www.sanipro.iit).
Solublon (Toyohashi Japan, http://www.solublon.com).
SPI Pharma (Delaware, http://www.spipharma.com).
Travelers Passport Paper Soap Sheets (http://www.weddingflavornow.com/index.asp?PageAction=VIEWPROD&PROD&ProdID=510).
Vaughan, C.D. "Solubility, Effects in Product, Package, Penetration and Preservation", Cosmetics and Toiletries, vol. 103, Oct. 1988, 24 pgs.
Vesterby, A.: "Star Volume in Bone Research: A Histomorphometric Analysis Of Trabecular Bone Structure Using Vertical Sections", Anal Rec: Feb. 1993, 232(2), pp. 325-334.
Wenda (China, http://www.wenda.com).
Wermuth et al. Drug Discovery, "Drug Discovery Today, 2006", vol. 11 7/8, 348-354, Year 2006.
Zhang et al. "Study on Morphology of Electrospun Poly( vinyl alcohol) Mats," European Polymer Journal 41 (2005), pp. 423-432.
Hiroshi Yagi & 4 Others, Research Study of a Friction Protector for Preventing a Tow Line From Breaking, Working Papers for Fiscal 2006 | Japan | Japan Coast Guard Dec. 2007, pp. 1-8.
Latorre Carmen, Nanotribological Effects of Hair Careproducts and Environment on Human Hair Using Atomic Forcemicroscopy,Journal of Vacuum Science and Technology: Part A, U.S.A, AVS/AIP , Jun. 28, 2005 , V2 3 N 4, p. 1034-1045.
Pattama Taepaiboon, et al., "Effect of Cross-linking on Properties and Release Characteristics of Sodium Salicylate-loaded Electrospun Poly(Vinyl Alcohol) Fibre Mats", Nanotechnology, vol. 18, No. 17, Apr. 2, 2007.
Wikipedia "Polyvinyl alcohol," last modified Mar. 30, 2017; https://en.wikipedia.org/wiki/Polyvinyl_alcohol.
"Prill", wikipedia, https://en.wikipedia.org/wiki/Prill, No Known date, 1 Page.

\* cited by examiner

CONDITIONING HAIR CARE COMPOSITIONS IN THE FORM OF DISSOLVABLE SOLID STRUCTURES

FIELD OF THE INVENTION

The present invention relates to conditioning hair care compositions in the form of dissolvable solid structures. The dissolvable solid structures comprise a polymeric structurant, a fatty amphiphiles and a cationic surfactant.

BACKGROUND OF THE INVENTION

Many personal care and other consumer products in the market today are sold in liquid form. While widely used, liquid products often have tradeoffs in terms of packaging, storage, transportation, and convenience of use. Liquid consumer products typically are sold in bottles which add cost as well as packaging waste, much of which ends up in land-fills.

Hair Care products in the form of a dissolvable solid structures present an attractive form to consumers. Market executions of dissolvable solid structures may include, dissolvable films, compressed powders in a solid, fibrous structures, porous foams, soluble deformable solids, powders, etc. However, many of these executions have consumer negatives during in use experience. For example, these products typically do not provide sufficient wet and dry conditioning to the hair. Products such as bars or prills, do not hydrate fast enough in the shower to satisfy the consumer's desire to quickly apply to the hair without undue effort to dissolve the product.

A need therefore still exists for dissolvable solid structures which deliver the desired wet and dry conditioning to the hair, and to improve the dissolving properties of the solid product to facilitate improved consumer in use satisfaction. A need also exists for a dissolvable solid structure that is not in a lamellar state when dry, yet yields a lamellar state upon wetting.

SUMMARY OF THE INVENTION

A dissolvable solid structure comprising: a fibrous material comprising; from about 1 wt % to about 50 wt % of a polymeric structurant; from about 10 wt % to about 85 wt % of one or more high melting point fatty material having a carbon chain length C12-C22 or mixtures thereof, wherein the melting point is above 25 C; from about 1 wt % to about 60 wt % of a cationic surfactant; wherein the polymeric structurant has a weight average molecular weight of from about 10,000 to about 6,000,000 g/mol, and wherein the components of the fibrous material form a homogenous material when molten, and wherein a lamellar structure is formed upon addition of water to the dissolvable solid structure in the ratio of about 5:1.

DETAILED DESCRIPTION OF THE INVENTION

A. Definitions

As used herein, The Dissolvable Solid Structure may be referred to herein as "the Dissolvable Solid Structure", "the Structure", or "the Dissolvable Structure".

As used herein, "dissolvable" means that the Dissolvable Solid Structure is completely soluble in water or it provides a uniform dispersion upon mixing in water according to the hand dissolution test. The Dissolvable Solid Structure has a hand dissolution value of from about 1 to about 30 strokes, alternatively from about 2 to about 25 strokes, alternatively from about 3 to about 20 strokes, and alternatively from about 4 to about 15 strokes, as measured by the Hand Dissolution Method.

As used herein, "flexible" means a Dissolvable Solid Structure meets the distance to maximum force values discussed herein.

Figure 1:
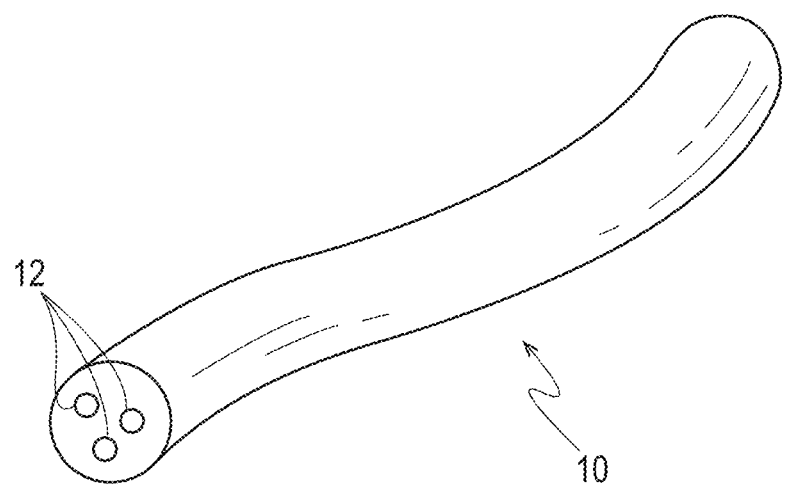
FIG. 1 is a schematic representation of an example of a fibrous element, in this case a filament, according to the present invention.

"Fibrous structure" as used herein means a structure that comprises one or more fibrous elements and optionally, one or more particles. The fibrous structure as described herein can mean an association of fibrous elements and optionally, particles that together form a structure, such as a unitary structure, capable of performing a function. For example, as shown in FIG. 1, a fibrous element, such as a filament 10 made from a fibrous element-forming composition such that one or more additives 12, for example one or more active agents, may be present in the filament rather than on the filament, such as a coating composition comprising one or more active agents, which may be the same or different from the active agents in the fibrous elements and/or particles.

Figure 2:
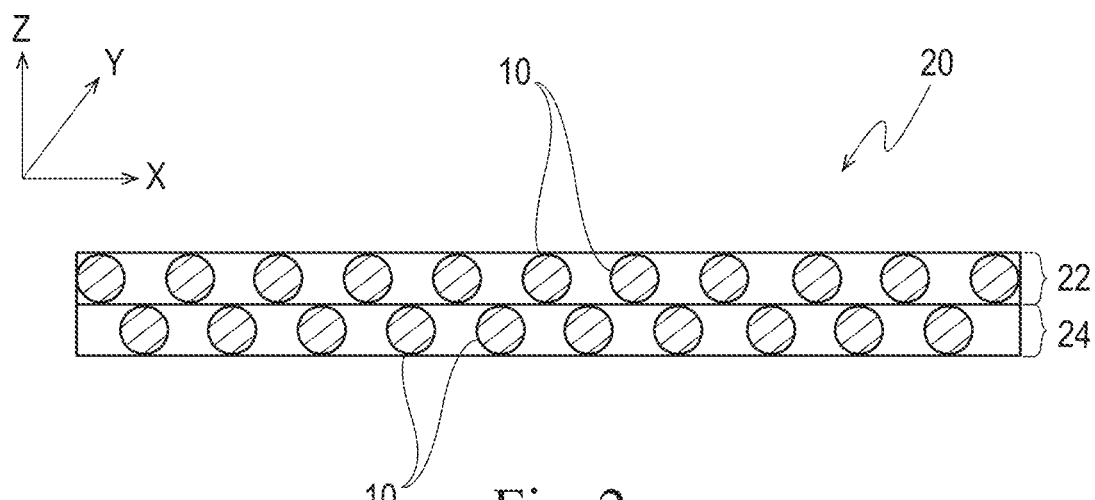
FIG. 2 is a schematic representation of an example of a fibrous structure comprising a plurality of filaments according to the present invention.

As shown in FIG. 2, an example of an dissolvable solid structure 20 of the present invention, for example a multi-ply fibrous structure according to the present invention may comprise two or more different fibrous structure layers or plies 22, 24 (in the z-direction of the dissolvable solid structure 20 of filaments 10 of the present invention that form the fibrous structures of the dissolvable solid structure 20. The filaments 10 in layer 22 may be the same as or different from the filaments 10 in layer 24. Each layer or ply 22, 24 may comprise a plurality of identical or substantially identical or different filaments. For example, filaments that may release their active agents at a faster rate than others within the dissolvable solid structure 20 and/or one or more fibrous structure layers or plies 22, 24 of the dissolvable solid structure 20 may be positioned as an external surface of the dissolvable solid structure 20. The layers or plies 22 and 24 may be associated with each other by mechanical entanglement at their interface between the two layers or plies and/or by thermal or adhesive bonding and/or by depositing one of the layers or plies onto the other existing layer or ply, for example spinning the fibrous elements of layer or ply 22 onto the surface of the layer or ply 24.

Figure 3:
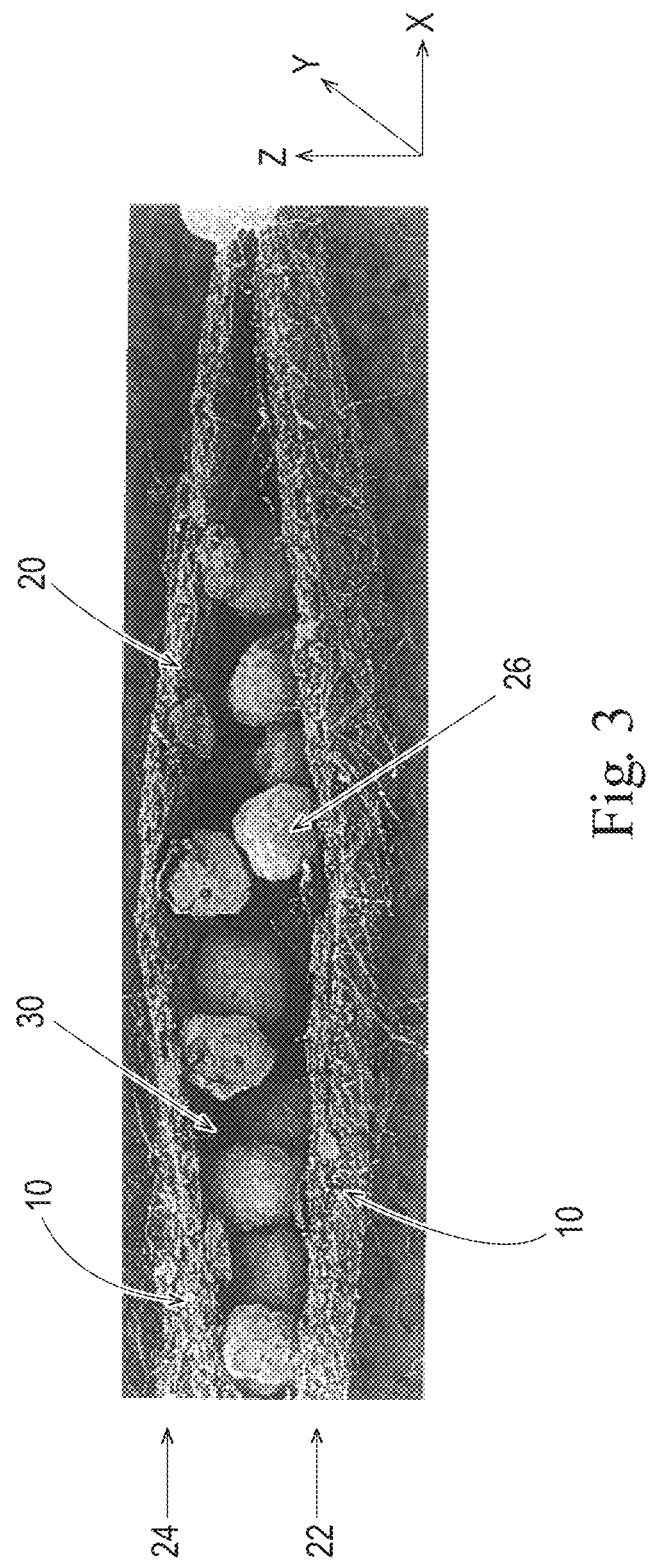
FIG. 3 is a scanning electron microscope photograph of a cross-sectional view of an example of a fibrous structure according to the present invention.

As shown in FIG. 3, another example of an dissolvable solid structure 20, for example a fibrous structure according to the present invention comprises a first fibrous structure layer or ply 22 comprising a plurality of fibrous elements, for example filaments 10, a second fibrous structure layer 24 comprising a plurality of fibrous elements, for example filaments 10, and a plurality of particles or a particle layer 26 positioned between the first and second fibrous structure layers 22 and 24. A similar fibrous structure can be formed by depositing a plurality of particles on a surface of a first ply of fibrous structure comprising a plurality of fibrous elements and then associating a second ply of fibrous structure comprising a plurality of fibrous elements such that the particles or a particle layer are positioned between the first and second fibrous structure plies.

Figure 4:
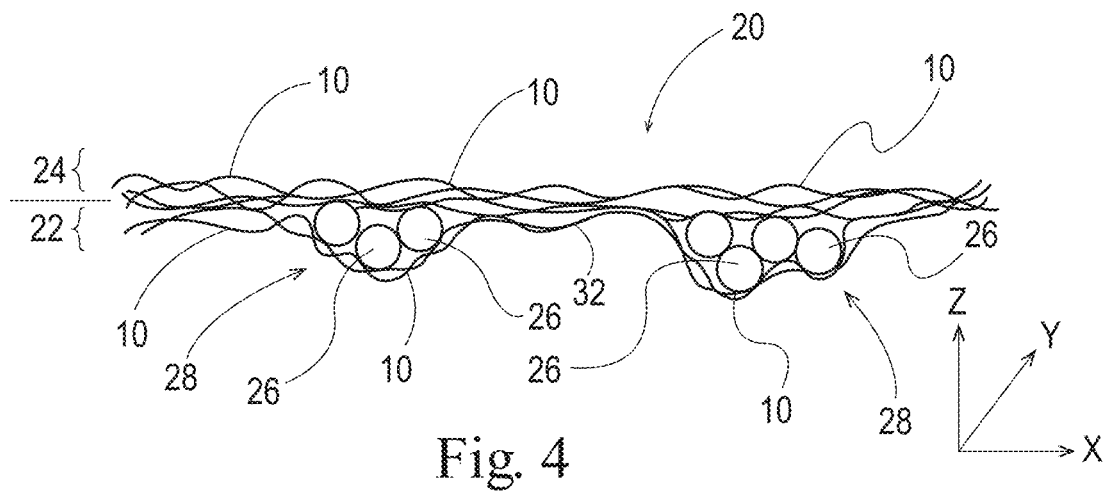
FIG. 4 is a schematic representation of a cross-sectional view of another example of a fibrous structure according to the present invention.

As shown in FIG. 4, another example of an dissolvable solid structure 20, for example a fibrous structure of the present invention comprises a first fibrous structure layer 22 comprising a plurality of fibrous elements, for example filaments 10, wherein the first fibrous structure layer 22 comprises one or more pockets 28 (also referred to as recesses, unfilled domes, or deflected zones), which may be in an irregular pattern or a non-random, repeating pattern. One or more of the pockets 28 may contain one or more particles 26. The dissolvable solid structure 20 in this example further comprises a second fibrous structure layer 24 that is associated with the first fibrous structure layer 22 such that the particles 26 are entrapped in the pockets 28. Like above, a similar dissolvable solid structure can be formed by depositing a plurality of particles in pockets of a first ply of fibrous structure comprising a plurality of fibrous elements and then associating a second ply of fibrous structure comprising a plurality of fibrous elements such that the particles are entrapped within the pockets of the first ply. In one example, the pockets may be separated from the fibrous structure to produce discrete pockets.

Figure 5:
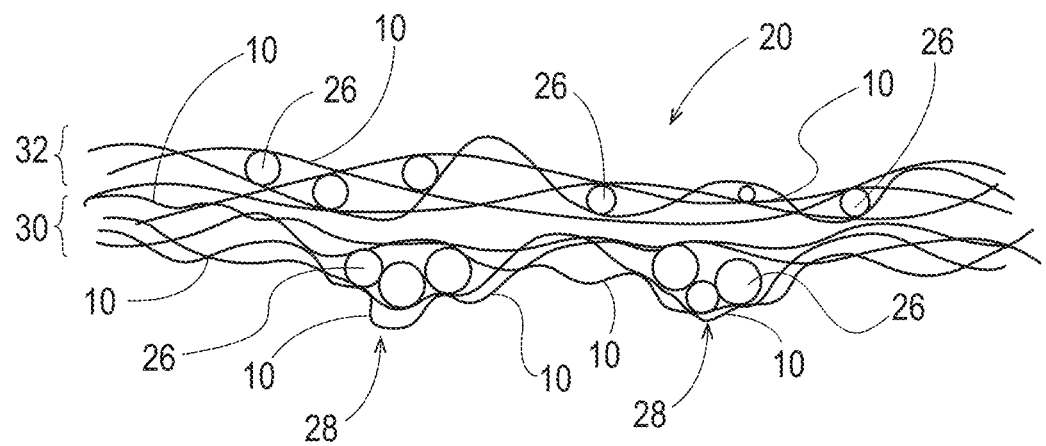
FIG. 5 is a schematic representation of a cross-sectional view of another example of a fibrous structure according to the present invention.

As shown in FIG. 5, another example of an dissolvable solid structure 20, for example a multi-ply fibrous structure of the present invention comprises a first ply 30 of a fibrous structure according to FIG. 4 above and a second ply 32 of fibrous structure associated with the first ply 30, wherein the second ply 32 comprises a plurality of fibrous elements, for example filaments 10, and a plurality of particles 26 dispersed, in this case randomly, in the x, y, and z axes, throughout the dissolvable solid structure 20.

Figure 6:
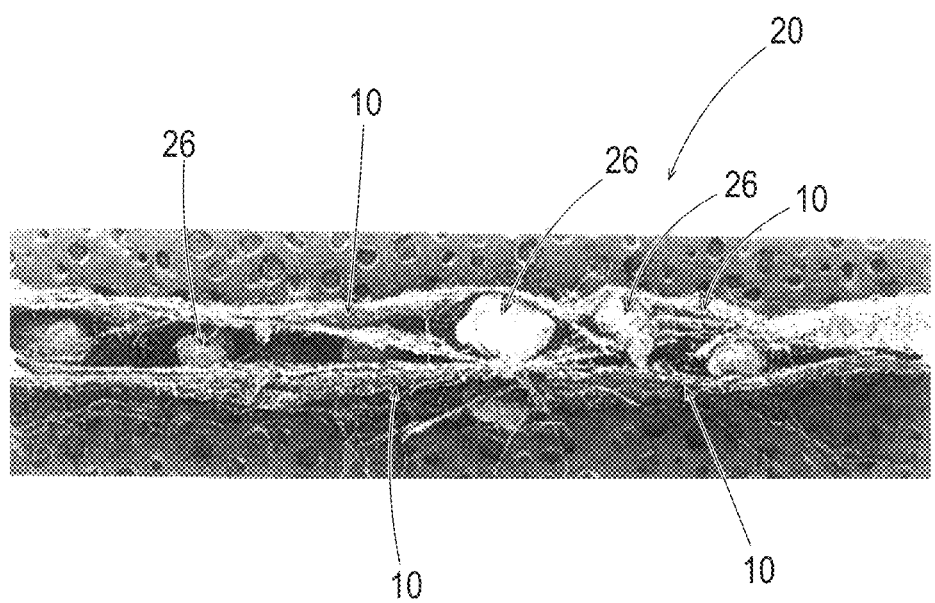
FIG. 6 is a scanning electron microscope photograph of a cross-sectional view of another example of a fibrous structure according to the present invention.

As shown in FIG. 6, another example of an dissolvable solid structure 20, for example a fibrous structure of the present invention comprises a plurality of fibrous elements, for example filaments 10, such as active agent-containing filaments, and a plurality of particles 26, for example active agent-containing particles, dispersed, in this case randomly, in the x, y, and z axes, throughout the fibrous structure of the dissolvable solid structure 20.

Figure 7:
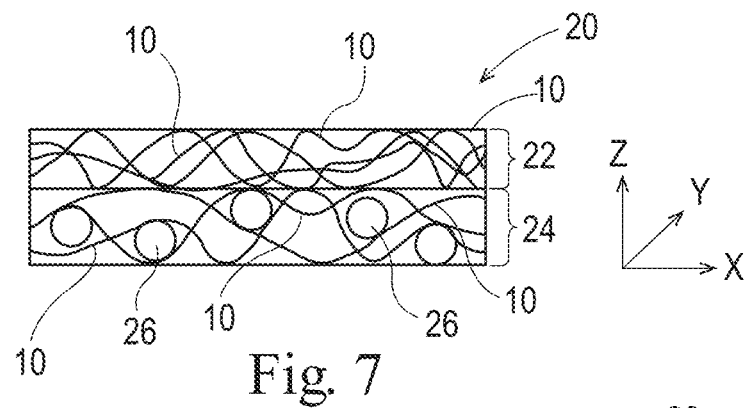
FIG. 7 is a schematic representation of a cross-sectional view of another example of a fibrous structure according to the present invention.

As shown in FIG. 7, another example of an dissolvable solid structure 20, for example a fibrous structure of the present invention comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24. Alternatively, in another embodiment, the plurality of particles 26, for example active agent-containing particles, may be dispersed in an irregular pattern or a non-random, repeating pattern within the second fibrous structure layer 24. Like above, a similar dissolvable solid structure comprising two plies of fibrous structure comprising a first fibrous structure ply 22 comprising a plurality of fibrous elements, for example filaments 10, and a second fibrous structure ply 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure ply 24. Alternatively, in another embodiment, the plurality of particles 26, for example active agent-containing particles, may be dispersed in an irregular pattern or a non-random, repeating pattern within the second fibrous structure ply 24.

Figure 8:
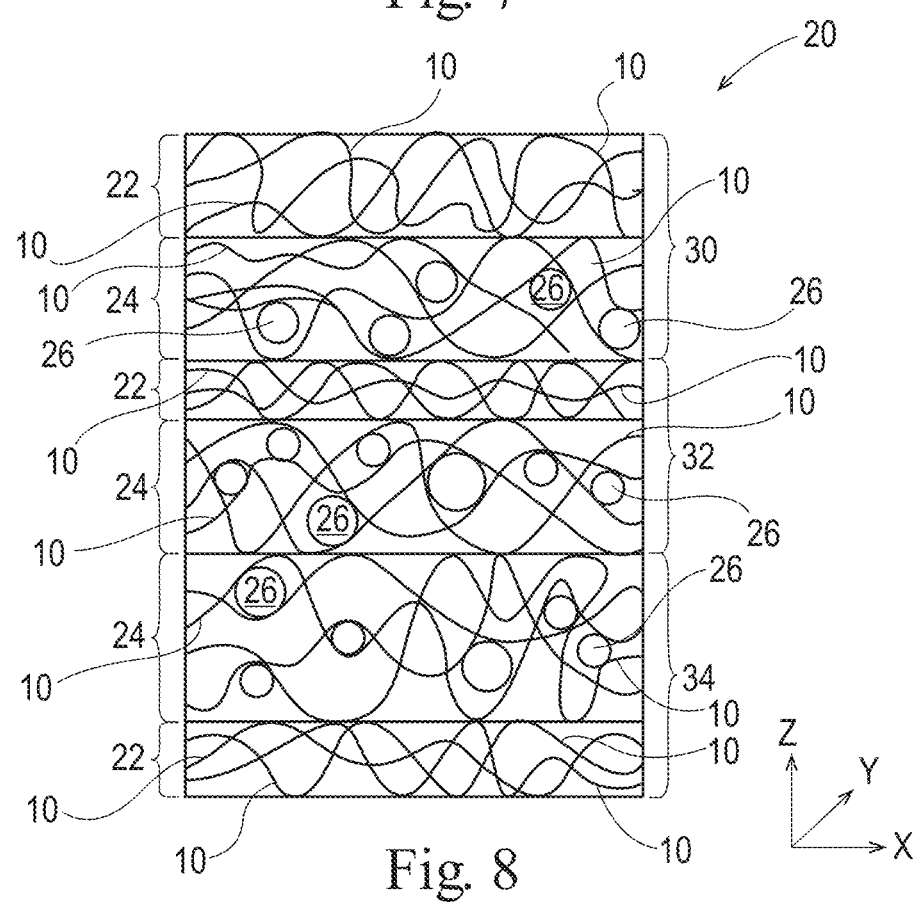
FIG. 8 is a schematic representation of a cross-sectional view of another example of a fibrous structure according to the present invention.

FIG. 8 shows another example of an dissolvable solid structure 20, for example a multi-ply fibrous structure of the present invention comprising a first ply 30 of a fibrous structure as shown in FIG. 7 comprising a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, a second ply 32 of a fibrous structure associated with the first ply 30, wherein the second ply 32 comprises a first fibrous structure layer 22 comprising a plurality of fibrous elements, for example filaments 10, and a second layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, and a third ply 34 of a fibrous structure associated with the second ply 32, wherein the third ply 34 comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24.

Figure 9:
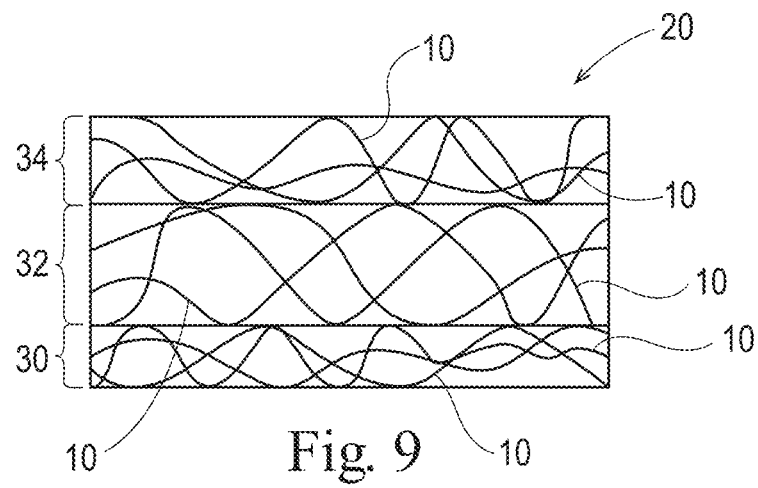
FIG. 9 is a schematic representation of a cross-sectional view of another example of a fibrous structure according to the present invention.

As shown in FIG. 9, another example of an dissolvable solid structure 20, for example a multi-ply fibrous structure of the present invention comprises a first ply 30 of a fibrous structure comprising a plurality of fibrous elements, for example filaments 10, a second ply 32 of a fibrous structure associated with the first ply 30, wherein the second ply 32 comprises a plurality of fibrous elements, for example filaments 10, and a third ply 34 of a fibrous structure associated with the second ply 32, wherein the third ply 34 comprises a plurality of fibrous elements, for example filaments 10. In one embodiment of FIG. 9, each ply's filaments 10 may comprise active agent-containing filaments.

Figure 10:
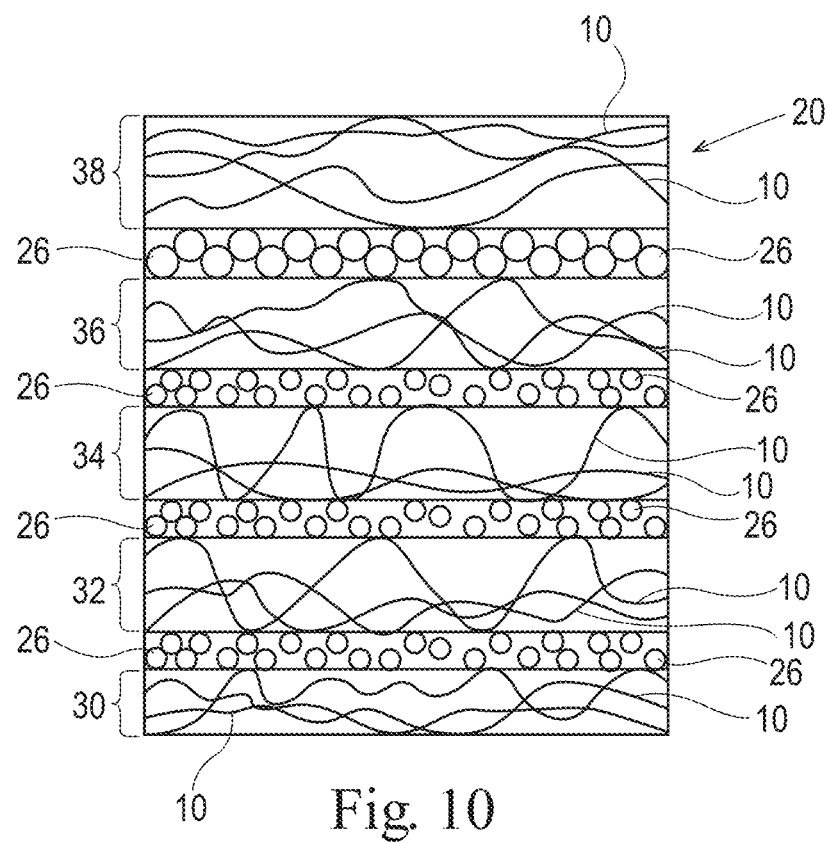
FIG. 10 is a schematic representation of a cross-sectional view of another example of a fibrous structure according to the present invention.

FIG. 10 shows another example of an dissolvable solid structure 20 multi-ply fibrous structure 20 of the present invention comprising a first ply 30 of a fibrous structure comprising a plurality of fibrous elements, for example filaments 10, a second ply 32 of fibrous structure comprising a plurality of fibrous elements, for example filaments 10, a third ply 34 of a fibrous structure comprising a plurality of fibrous elements, for example filaments 10, a fourth ply 36 of fibrous structure comprising a plurality of fibrous elements, for example filaments 10, and a fifth ply 38 of a fibrous structure comprising a plurality of fibrous elements, for example filaments 10. In this example, the dissolvable solid structure 20 further comprises one or more particles or particle layers 26 positioned between at least two adjacent fibrous structure plies, for example plies 30 and 32 or plies 32 and 34 or plies 34 and 36 or plies 36 and 38. The plies 30, 32, 34, 36, and 38 are associated with one or more other plies to form a unitary structure and to minimize particles 26, if any are present within the dissolvable solid structure 20, from becoming disassociated from the dissolvable solid structure 20. In another embodiment, the one or more particles or particle layers 26 positioned between at least two adjacent fibrous structure plies are present in an irregular pattern, a non-random, repeating pattern, or only in select zones between the plies.

The fibrous structures of the present invention may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layers. A layer may comprise a particle layer within the fibrous structure or between fibrous element layers within a fibrous structure. A layer comprising fibrous elements may sometimes be referred to as a ply. A ply may be a fibrous structure which may be homogeneous or layered as described herein.

The single-ply fibrous structure or a multi-ply fibrous structure comprising one or more fibrous structure plies as described herein may exhibit a basis weight of less than 5000 g/m$^2$ as measured according to the Basis Weight Test Method described herein. For example, the single- or multi-ply fibrous structure according to the present invention may exhibit a basis weight of greater than 10 g/m$^2$ to about 5000 g/m$^2$ and/or greater than 10 g/m$^2$ to about 3000 g/m$^2$ and/or greater than 10 g/m$^2$ to about 2000 g/m$^2$ and/or greater than 10 g/m$^2$ to about 1000 g/m$^2$ and/or greater than 20 g/m$^2$ to about 800 g/m$^2$ and/or greater than 30 g/m$^2$ to about 600 g/m$^2$ and/or greater than 50 g/m$^2$ to about 500 g/m$^2$ and/or greater than 300 g/m$^2$ to about 3000 g/m$^2$ and/or greater than 500 g/m$^2$ to about 2000 g/m$^2$ as measured according to the Basis Weight Test Method.

In one example, the fibrous structure of the present invention is a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two or more different fibrous elements.

"Article" as used herein refers to a consumer use unit, a consumer unit dose unit, a consumer use saleable unit, a single dose unit, or other use form comprising a unitary fibrous dissolvable solid structure and/or comprising one or more fibrous structures of the present invention.

"Fibrous element" as used herein means an elongated particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from a filament-forming compositions also referred to as fibrous element-forming compositions via suitable spinning process operations, such as meltblowing, spunbonding, electro-spinning, and/or rotary spinning.

The fibrous elements of the present invention may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongated particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol and also thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongated particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element of the present invention such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

In one example as shown in FIG. 1, a fibrous element, for example a filament 10 of the present invention made from a fibrous element-forming composition of the present invention is such that one or more additives 12, for example one or more active agents, may be present in the filament rather than on the filament, such as a coating composition comprising one or more active agents, which may be the same or different from the active agents in the fibrous elements and/or particles. The total level of fibrous element-forming materials and total level of active agents present in the fibrous element-forming composition may be any suitable amount so long as the fibrous elements of the present invention are produced therefrom.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

"Filament-forming material" and/or "fibrous element-forming material" as used herein means a material, such as a polymer or monomers capable of producing a polymer that exhibits properties suitable for making a fibrous element. In one example, the filament-forming material comprises one or more substituted polymers such as an anionic, cationic, zwitterionic, and/or nonionic polymer. In another example, the polymer may comprise a hydroxyl polymer, such as a polyvinyl alcohol ("PVOH"), polyvinylpyrrolidone ("PVP"), polydimethyl acrylamide, a partially hydrolyzed polyvinyl acetate and/or a polysaccharide, such as starch and/or a starch derivative, such as an ethoxylated starch and/or acid-thinned starch, carboxymethylcellulose, hydroxypropyl cellulose, hydroxyethyl cellulose. In yet another example, the filament-forming material is a polar solvent-soluble material.

As used herein, "porous" means that the Dissolvable Solid Structure has spaces, voids or interstices, (generally referred to herein as "pores") provided by the microscopic complex three-dimensional configuration, that provide channels, paths or passages through which a liquid can flow.

As used herein, "porosity" and "percent porosity" are used interchangeably and each refers to a measure of void volume of the Dissolvable Solid Structure and is calculated as

[1−([basis weight of Dissolvable Solid Structure]/
[thickness of Dissolvable Solid Structure X
density of the bulk, dried material])]×100% with the units adjusted so they cancel and multiplied by 100% to provide percent porosity.

The Dissolvable Solid Structure may be referred to herein as "the Dissolvable Solid Structure" or "the Dissolvable Structure".

As used herein, "vinyl pyrrolidone copolymer" (and "copolymer" when used in reference thereto) refers to a polymer of the following structure (I): (I)

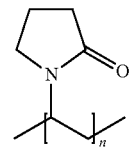

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers.

The term "molecular weight" or "Molecular weight" refers to the weight average molecular weight unless otherwise stated. Molecular weight is measured using industry standard method, gel permeation chromatography ("GPC").

As used herein, the articles including "a" and "an" when used in a claim, are understood to mean one or more of what is claimed or described.

As used herein, the terms "include," "includes," and "including," are meant to be non-limiting.

The methods disclosed in the Test Methods Section of the present application should be used to determine the respective values of the parameters of Applicants' inventions, including those discussed in the Dissolvable Structures—Physical Characteristics section below.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

B. Dissolvable Solid Structure

Hair Care products in the form of a dissolvable solid structure present an attractive form to consumers. A typical use of these products includes a consumer holding the product in her hand, adding water to create a solution or dispersion and applying to the hair. In many cases, the products can take a long time to dissolve making it a less enjoyable experience for the consumer. Therefore, a need exists to have dissolvable solids that exhibit more rapid dissolution. Additionally, it is desirable to have a dissolvable solid structure that forms a lamellar structure upon addition of water to the dissolvable solid structure in the ratio of about 5:1.

Dissolvable Structures—Compositional

The Dissolvable Solid Structure as described herein can be in the form of a fibrous structure comprising: (a) from about 1 wt % to about 50 wt % polymeric structurant; (b) from about 10 wt % to about 85 wt % of a high melting point fatty compound such as a fatty amphiphile, and (c) from about 1 wt % to about 60 wt % of a cationic surfactant. When water is added to the dissolvable solid structure at a ratio of about 5:1 a lamellar structure is formed.

Polymeric Structurant

To improve the fiber spinning of low viscosity material, such as molten fatty alcohols, fatty quaternary ammonium compounds, fatty acids, etc., a polymeric ingredient called a structurant is added. The structurant increases the shear and extensional viscosity of the fluid to enable fiber formation. The structurant can be included at a level of from about 1 wt % to about 50 wt %, alternatively from about 1 wt % to about 30 wt %, alternatively from about 1 wt % to about 10 wt %, alternatively from about 2 wt % to about 6 wt %, and alternatively from about 3 wt % to about 5 wt % of the composition. The structurant has a weight average molecular weight of from about 10,000 to about 6,000,000 g/mol. The weight average molecular weight is computed by summing the average molecular weights of each polymer raw material multiplied by their respective relative weight percentages by weight of the total weight of polymers present within the Dissolvable Solid Structure. However, a balance is often struck between concentration and molecular weight, such that when a lower molecular weight species is used, it requires a higher level to result in optimal fiber spinning. Likewise, when a higher molecular species is used, lower levels can be used to achieve optimal fiber spinning. The structurant having a weight average molecular weight of from about 3,000,000 g/mol to about 5,000,000 g/mol in included at a level of from about 3 wt % to about 6 wt %. Alternatively, a structurant having a weight average molecular weight of from about 50,000 g/mol to about 100,000 g/mol can be included at a level of from about 30 wt % to about 50 wt %. The structurant is soluble in an oily mixture to enable viscosity build for fiber spinning. In addition, the structurant should also be soluble in water to promote removal and to prevent buildup. Suitable structurants include, but are not limited to, polyvinylpyrrolidone, polydimethylacrylamides, and combinations thereof. These polymers are oil (fatty alcohol, fatty acid, fatty quaternary ammonium compounds) soluble, water soluble, and capable of being produced at high weight average molecular weights. For example, suitable polymers for use are PVP K120 from Ashland Inc., having a weight average molecular weight of about 3,500,000 g/mol is soluble in the oil and water and enables fibers to be formed and collected onto a belt. Additional suitable polymers include copolymers of polyvinylpyrrolidone, such as Ganex® or PVP/VA (weight average molecular weight of about 50,000 g/mol) copolymers from Ashland Inc., also performed as suitable structurants but a higher level was utilized to be effective due to their lower weight average molecular weight. In addition, copolymers of polydimethylacrylamide also function as a suitable structurant. Hydroxyl propyl cellulose can also function as a suitable structurant.

Dispersing Agents

When preparing dissolvable solid structure, it has been found that the addition of a dispersing agent greatly increases the wetting, hydration, and dispersion of the conditioner materials. The dispersing agent can be included at a level of from about 1 wt % to about 30 wt % of the composition, alternatively from about 5 wt % to about 15 wt %, and alternatively from about 5 wt % to about 10 wt %. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, cocoamiodpropyl betaines, alkyl glucoside, Triethanol amine, cocamide MEAs and mixtures thereof.

Cationic Surfactant

The dissolvable solid structure can comprise a cationic surfactant can be included at a level of from about 1 wt % to about 60 wt %, alternatively from about 10 wt % to about 50 wt %, alternatively from about 20 wt % to about 40 wt % of the composition.

Cationic surfactant useful herein can be one cationic surfactant or a mixture of two or more cationic surfactants. The cationic surfactant can be selected from the group consisting of, but not limited to: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt, a tertiary amine and combinations thereof.

Mono-Long Alkyl Amine

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines Primary, secondary, and tertiary fatty amines are useful.

Suitable for use in the dissolvable solid structure are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethyl amine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as $\ell$-glutamic acid, lactic acid, hydrochloric acid, malic acid, succinic acid, acetic acid, fumaric acid, tartaric acid, citric acid, $\ell$-glutamic hydrochloride, maleic acid, and mixtures thereof; alternatively $\ell$-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

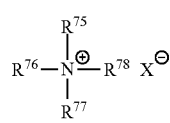

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof. Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (I):

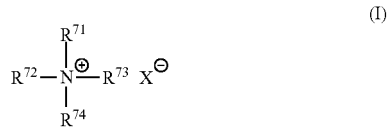

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 10 wt % to about 85 wt %, alternatively from 20 wt % to 70 wt %, alternatively from about 50 wt % to about 70 wt %, alternatively from about 10 wt % to about 20 wt % of the composition. The fatty compound can be selected from the group consisting of, but not limited to, fatty amphiphiles, fatty alcohol, fatty acid, fatty amide, fatty ester and combinations thereof.

The high melting point fatty compound useful herein have a melting point of 25° C. or higher, alternatively 40° C. or higher, alternatively 45° C. or higher, alternatively 50° C. or higher, in view of stability of the emulsion especially the gel matrix. Such melting point is up to about 90° C., alternatively up to about 80° C., alternatively up to about 70° C., alternatively up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, fatty amides, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols can be used in the composition described herein. The fatty alcohols useful herein are those having from about 14 to about 30 carbon atoms, alternatively from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

Generally, in the mixture, the weight ratio of cetyl alcohol to stearyl alcohol is from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of from about 1:1 to about 4:1, alternatively from about 1:1 to about 2:1, alternatively from about 1.2:1 to about 2:1, in view of maintaining acceptable consumer usage. It may also provide more conditioning on damaged part of the hair.

C. Optional Ingredients

The Structure (dried) optionally comprises from about 1 wt % to about 25 wt % plasticizer, in one embodiment from about 3 wt % to about 20 wt % plasticizer, in one embodiment from about 5 wt % to about 15 wt % plasticizer.

When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The Structure may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodetrins, polymer microcapsules, starch encapsulated accords and combinations thereof.

Suitable conditioning agents include high melting point fatty compounds, silicone conditioning agents and cationic conditioning polymers. Suitable materials are discussed in US 2008/0019935, US 2008/0242584 and US 2006/0217288.

Non-limiting examples of product type embodiments for use by the Structure include hand cleansing Structures, hair shampoo or other hair treatment Structures, body cleansing Structures, shaving preparation Structures, personal care Structures containing pharmaceutical or other skin care active, moisturizing Structures, sunscreen Structures, chronic skin benefit agent Structures (e.g., vitamin-containing Structures, alpha-hydroxy acid-containing Structures, etc.), deodorizing Structures, fragrance-containing Structures, and so forth.

For fibrous Structures, the Structure comprises a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 1% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 micron. The dissolvable fibers produced by the method of the present disclosure have a significant number of dissolvable fibers with an average diameter less than about 1 micron, or sub-micron fibers. In an embodiment, Dissolvable Solid Structure may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The percent porosity of the dissolvable solid Structure is at least about 25%, alternatively at embodiment at least about 50%, alternatively at least about 60%, alternatively at least about 70% and alternatively at least about 80%. The porosity of the dissolvable solid Structure is not more than about 99%, alternatively not more than about 98%, alternatively not more than about 95%, and alternatively not more than about 90%. Porosity of a Structure is determined according to the procedure set forth in the definition of "porosity" above.

A range of effective sizes of pores can be accommodated. The pore size distribution through the Structure cross-section may be symmetric or asymmetric.

The Structure can be flexible and have a distance to maximum force value of from about 6 mm to about 30 mm. The distance to maximum force value from about 7 mm to about 25 mm, alternatively from about 8 mm to about 20 mm, and alternatively from about 9 mm to about 15 mm.

The Structure can be characterized in one aspect by its Specific Surface Area. The Structure can have a Specific Surface Area of from about 0.03 $m^2/g$ to about 0.25 $m^2/g$, alternatively from about 0.035 $m^2/g$ to about 0.22 $m^2/g$, alternatively from about 0.04 $m^2/g$ to about 0.19 $m^2/g$, and alternatively from about 0.045 $m^2/g$ to about 0.16 $m^2/g$.

The Structure can be a flat, flexible Structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively two or more sheets are combined to form a Structure with a thickness of about 5 mm to about 10 mm.

The Structure can have a basis weight of from about 200 grams/$m^2$ to about 2,000 grams/$m^2$, alternatively from about 400 g/$m^2$ to about 1,200 g/$m^2$, alternatively from about 600 g/$m^2$ to about 2,000 g/$m^2$, and alternatively from about 700 g/$m^2$ to about 1,500 g/$m^2$.

The Structure can have a dry density of from about 0.08 g/$cm^3$ to about 0.40 g/$cm^3$, alternatively from about 0.08 g/$cm^3$ to about 0.38 g/$cm^3$, alternatively from about 0.10 g/$cm^3$ to about 0.25 g/$cm^3$, and alternatively from about 0.12 g/$cm^3$ to about 0.20 g/$cm^3$.

Methods of Manufacture—Fibrous Structures

The fibrous elements of the present invention may be made by any suitable process. A non-limiting example of a suitable process for making the fibrous elements is described below.

Figure 11:
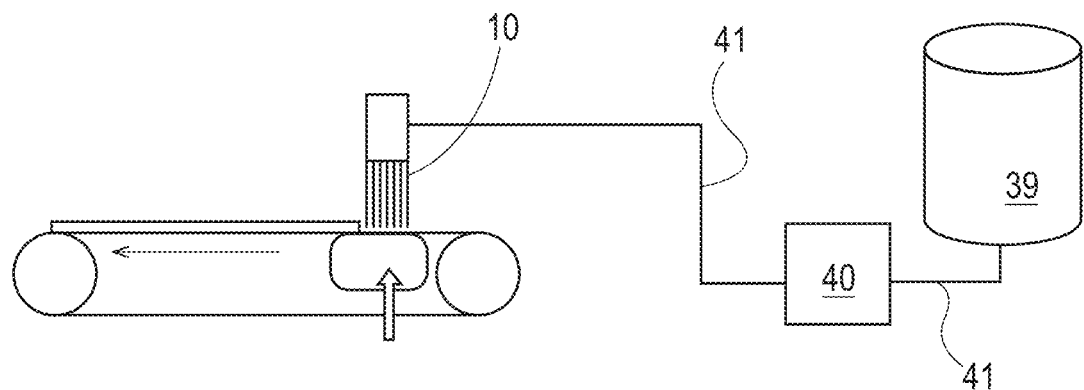
FIG. 11 is a schematic representation of an example of a process for making an example of a fibrous structure according to the present invention.
Figure 12:
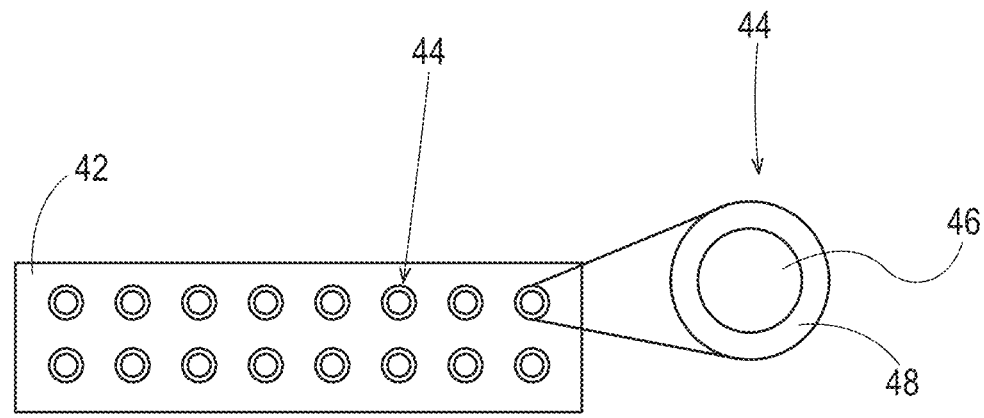
FIG. 12 is a schematic representation of an example of a die with a magnified view used in the process of FIG. 11.
Figure 13:
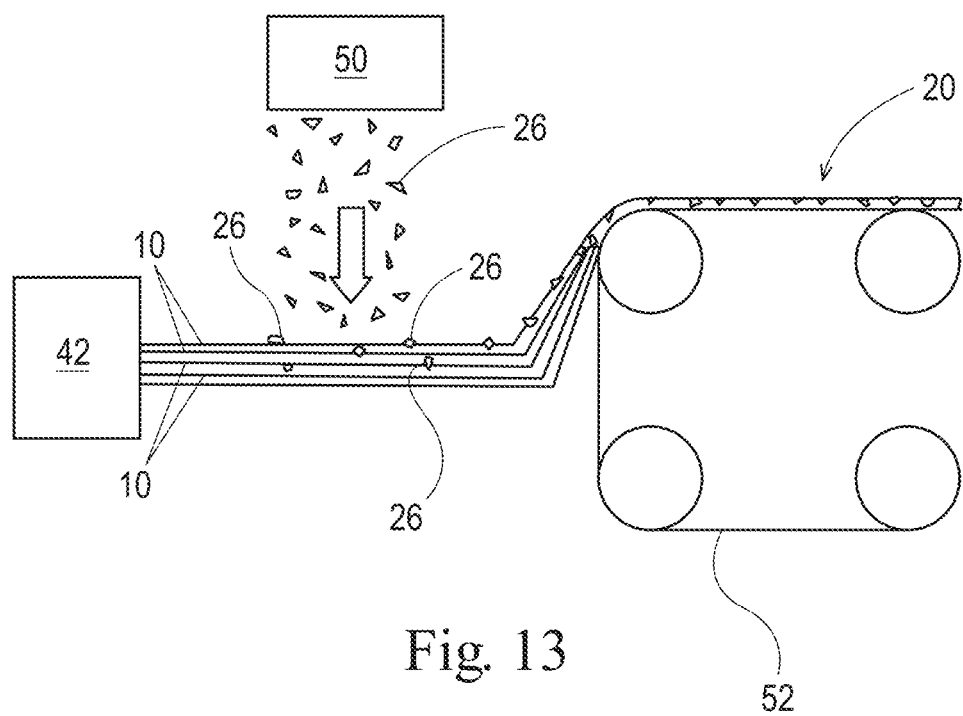
FIG. 13 is a schematic representation of an example of another process for making an example of a fibrous structure according to the present invention.

As shown in FIG. 13, a fibrous structure, for example a fibrous structure layer or ply 22 of the present invention may be made by spinning a filament-forming composition from a spinning die 42, as described in FIGS. 11 and 12, to form a plurality of fibrous elements, such as filaments 10, and then optionally, associating one or more particles 26 provided by a particle source 50, for example a sifter or an airlaid forming head. The particles 26 may be dispersed within the fibrous elements, for example filaments 10. The mixture of particles 26 and fibrous elements, for example filaments 10 may be collected on a collection belt 52, such as a patterned collection belt that imparts a texture, such as a three-dimensional texture to at least one surface of the fibrous structure layer or ply 22.

Figure 14:
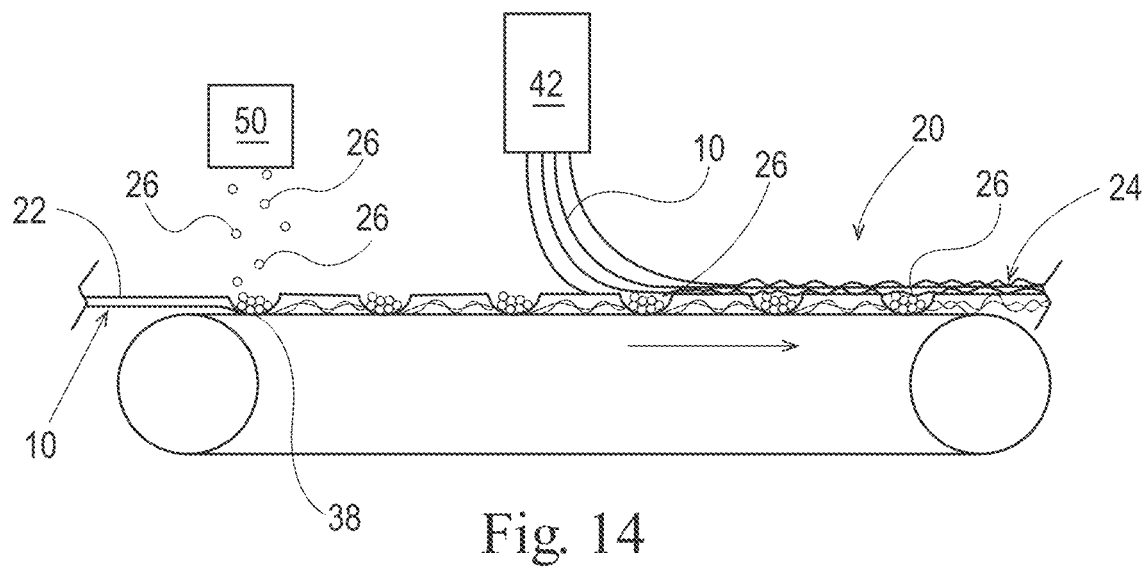
FIG. 14 is a schematic representation of another example of a process for making another example of a fibrous structure according to the present invention.

FIG. 14 illustrates an example of a method for making a dissolvable solid structure 20 according to FIG. 4. The method comprises the steps of forming a first fibrous structure layer 22 of a plurality of fibrous elements, for example filaments 10 such that pockets 28 are formed in a surface of the first fibrous structure layer 22. One or more particles 26 are deposited into the pockets 28 from a particle source 50.

A second fibrous structure layer 24 comprising a plurality of fibrous elements, for example filaments 10 produced from a spinning die 42 are then formed on the surface of the first fibrous structure layer 22 such that the particles 26 are entrapped in the pockets 28.

Figure 15:
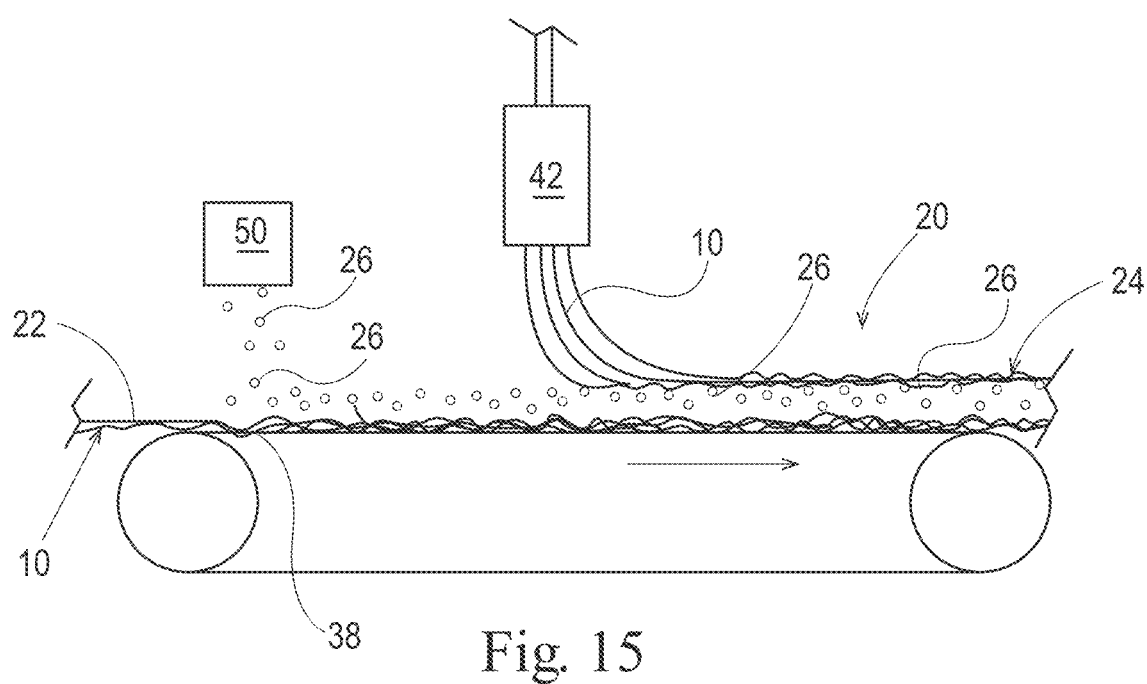
FIG. 15 is a schematic representation of another example of a process for making another example of a fibrous structure according to the present invention.

FIG. 15 illustrates yet another example of a method for making a dissolvable solid structure 20 according to FIG. 3. The method comprises the steps of forming a first fibrous structure layer 22 of a plurality of fibrous elements, for example filaments 10. One or more particles 26 are deposited onto a surface of the first fibrous structure layer 22 from a particle source 50. A second fibrous structure layer 24 comprising a plurality of fibrous elements, for example filaments 10 produced from a spinning die 42 are then formed on top of the particles 26 such that the particles 26 are positioned between the first fibrous structure layer 22 and the second fibrous structure layer 24.

Figure 16:
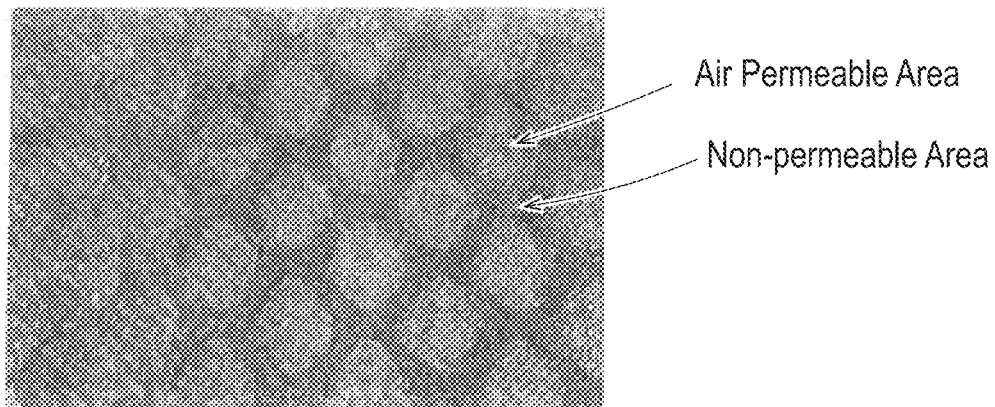
FIG. 16 is a representative image of an example of a patterned belt useful in the processes for making the fibrous structure according to the present invention.

The dry embryonic fibrous elements, for example filaments may be collected on a molding member as described above. The construction of the molding member may provide areas that are air-permeable due to the inherent construction. The filaments that are used to construct the molding member will be non-permeable while the void areas between the filaments will be permeable. Additionally a pattern may be applied to the molding member to provide additional non-permeable areas which may be continuous, discontinuous, or semi-continuous in nature. A vacuum used at the point of lay down is used to help deflect fibers into the presented pattern. An example of one of these molding members is shown in FIG. 16.

In addition to the techniques described herein in forming regions within the fibrous structures having a different properties (e.g., average densities), other techniques can also be applied to provide suitable results. One such example includes embossing techniques to form such regions. Suitable embossing techniques are described in U.S. Patent Application Publication Nos. 2010/0297377, 2010/0295213, 2010/0295206, 2010/0028621, and 2006/0278355.

In a multi-ply dissolvable solid structure, one or more fibrous structure plies may be formed and/or deposited directly upon an existing ply of fibrous structure to form a multi-ply fibrous structure. The two or more existing fibrous structure plies may be combined, for example via thermal bonding, gluing, embossing, aperturing, rotary knife aperturing, die cutting, die punching, needle punching, knurling, pneumatic forming, hydraulic forming, laser cutting, tufting, and/or other mechanical combining process, with one or more other existing fibrous structure plies to form the multi-ply dissolvable solid structure described herein.

Pre-formed dissolvable fibrous web (comprised of dissolvable fibers and, optionally, agglomerate particles), having approximately ⅓ the total desired basis weight of the finished dissolvable solid structure, can be arranged in a face to face relationship with post-add minor ingredients disposed between layers, and laminated with a solid state formation process. The resulting laminate is cut into the finished dissolvable solid structure shape via die cutting.

Lamination and Formation of Apertures via Solid State Formation

The 3-layer web stack with minors disposed between layers can be passed together through a solid state formation process (see Rotary Knife Aperturing apparatus below), forming roughly conical apertures in the dissolvable solid structure and causing inter-layer fiber interactions which result in a mechanically lamination dissolvable solid structure. Lamination aids (e.g. web plasticizing agents, adhesive fluids, etc.) may be additionally used to aid in secure lamination of layers.

Rotary Knife Aperturing Apparatus

Suitable solid state description in disclosed in U.S. Pat. No. 8,679,391. Also, suitable dissolvable web aperturing description is disclosed in US 2016/0101026 A1.

The nip comprises (2) intermeshed 100 pitch toothed rolls The teeth on the toothed rolls have a pyramidal shape tip with six sides that taper from the base section of the tooth to a sharp point at the tip. The base section of the tooth has vertical leading and trailing edges and is joined to the pyramidal shape tip and the surface of the toothed roller. The teeth are oriented so the long direction runs in the MD.

The teeth are arranged in a staggered pattern, with a CD pitch P of 0.100 inch (2.5 mm) and a uniform tip to tip spacing in the MD of 0.223 inch (5.7 mm). The overall tooth height TH (including pyramidal and vertical base sections) is 0.270 inch (6.9 mm), the side wall angle on the long side of the tooth is 6.8 degrees and the side wall angle of the leading and trailing edges of the teeth in the pyramidal tip section is 25 degrees.

Opposing rollers are aligned such that the corresponding MD rows of each roller are in the same plane and such that the pins intermesh in a gear-like fashion with opposing pins passing near the center of the space between pins in the opposing roller MD row of pins. The degree of interference between the virtual cylinders described by the tips of the pins is described as the Depth of Engagement.

As web passes through the nip formed between the opposing rollers, the teeth from each roller engage with and penetrate the web to a depth determined largely by the depth of engagement between the rollers and the nominal thickness of the web.

E. The Optional Preparing of the Surface Resident Coating Comprising the Active Agent The preparation of the surface resident coating comprising the active agent may include any suitable mechanical, chemical, or otherwise means to produce a composition comprising the active agent(s) including any optional materials as described herein, or a coating from a fluid.

Optionally, the surface resident coating may comprise a water releasable matrix complex comprising active agent(s). The water releasable matrix complexes can comprising active agent(s) are prepared by spray drying wherein the active agent(s) is dispersed or emulsified within an aqueous composition comprising the dissolved matrix material under high shear (with optional emulsifying agents) and spray dried into a fine powder. The optional emulsifying agents can include gum arabic, specially modified starches, or other tensides as taught in the spray drying art (See Flavor Encapsulation, edited by Sara J. Risch and Gary A. Reineccius, pages 9, 45-54 (1988), which is incorporated herein by reference). Other known methods of manufacturing the water releasable matrix complexes comprising active agent(s) may include but are not limited to, fluid bed agglomeration, extrusion, cooling/crystallization methods and the use of phase transfer catalysts to promote interfacial polymerization. Alternatively, the active agent(s) can be adsorbed or absorbed into or combined with a water releasable matrix material that has been previously produced via a variety of mechanical mixing means (spray drying, paddle mixers, grinding, milling etc.). The water releasable matrix material in either pellet or granular or other solid-based form (and comprising any minor impurities as supplied by the supplier including residual solvents and plasticizers) may be ground or milled into a fine powder in the presence of the active agent(s) via a variety of mechanical means, for instance in a grinder or hammer mill.

Where the Dissolvable Solid Structure has a particulate coating, the particle size is known to have a direct effect on the potential reactive surface area of the active agents and thereby has a substantial effect on how fast the active agent delivers the intended beneficial effect upon dilution with water. In this sense, the active agents with smaller particle sizes tend to give a faster and shorter lived effect, whereas the active agents with larger particle sizes tend to give a slower and longer lived effect. The surface resident coatings may have a particle size from about 1 μm to about 200 μm, alternatively from about 2 μm to about 100 μm, and alternatively from about 3 μm to about 50 μm.

It can be helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling, blending, spray drying, etc. The resulting powder may also be blended with other inert powders, either of inert materials or other powder-active complexes, and including water absorbing powders as described herein.

The active agents may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the active agent particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the active agents, of the surface resident coating composition and with subsequent particle size reduction as per the procedure described above.

Where the coating is applied to the Structure as a fluid (such as by as a spray, a gel, or a cream coating), the fluid can be prepared prior to application onto the Structure or the fluid ingredients can be separately applied onto the Structure such as by two or more spray feed steams spraying separate components of the fluid onto the Structure.

Post-add minor ingredients can be applied to the surface of one or more web layers in the dissolvable solid structure, typically an interior surface. Individual minor ingredients may be applied together to a single selected surface or to separate surfaces. Minor ingredients may be applied to interior or exterior surfaces. In the present examples, minors were applied to the same interior surface, namely to one side of the middle of three layers.

Post-add ingredients in the present examples include fragrance and amodimethicone, both fluid at room temperature. Additional minor ingredients could include alternative conditioning agents, co-surfactants, encapsulated fragrance vehicles, rheology modifiers, etc. Minor ingredients could include fluids, particulates, pastes, or combinations.

In the present examples, fragrance is applied by atomizing through a spray nozzle (example Nordson EFD spray nozzle) and directing the resulting droplets of perfume to the target web surface, essentially uniformly over the surface.

In the present examples, amodimethicone is applied by expressing the fluid through an extrusion nozzle (example ITW-Dynatec UFD hot melt glue nozzle), comprising a series of orifices, approximately 500 microns in diameter and spaced at 2.5 mm, resulting in stripes of fluid extending the length of the target web surface.

Alternate fluid dispensing technologies, application patterns, and characteristic dimensions are contemplated.

Methods of Use

The compositions described herein may be used for cleaning and/or treating hair, hair follicles, skin, teeth, and the oral cavity. The method for treating these consumer substrates may comprise the steps of: a) applying an effective amount of the Structure to the hand, b) wetting the Structure with water to dissolve the solid, c) applying the dissolved material to the target consumer substrate such as to clean or treat it, and d) rinsing the diluted treatment composition from the consumer substrate. These steps can be repeated as many times as desired to achieve the desired cleansing and or treatment benefit.

A method useful for providing a benefit to hair, hair follicles, skin, teeth, and/or the oral cavity, includes the step of applying a composition according to the first embodiment to these target consumer substrates in need of regulating.

Alternatively a useful method for regulating the condition of hair, hair follicles, skin, teeth, the oral cavity, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the dissolvable solid structures include hand cleansing substrates, teeth cleaning or treating substrates, oral cavity substrates, hair shampoo or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more dissolvable solid structures described herein, and a communication directing a consumer to dissolve the Structure and apply the dissolved mixture to hair, hair follicles, skin, teeth, the oral cavity, to achieve a benefit to the target consumer substrate, a rapidly lathering foam, a rapidly rinsing foam, a clean rinsing foam, and combinations thereof. The communication may be printed material attached directly or indirectly to packaging that contains the dissolvable solid structure or on the dissolvable solid structure itself. Alternatively, the communication may be an electronic or a broadcast message that is associated with the article of manufacture. Alternatively, the communication may describe at least one possible use, capability, distinguishing feature and/or property of the article of manufacture.

Test Methods Method of Visual Homogeneity of Molten Composition In an appropriate container, the fatty amphiphile is heated to 90 C with agitation. If desired, the dispersing agent is then added under agitation and allowed to melt. The polymeric structurant is then added under agitation and allowed to melt. The cationic surfactant is then added to the molten mixture under agitation and allowed to melt. Final molten composition is allowed to dearate. Visual assessment of homogeneity is made as being either an optically clear, single phase composition or a uniform dispersion prior to fiber formation. Data is recorded as Yes or No.

Lamellar Structure Test Method

The Lamellar Structure Test Method makes use of small-angle x-ray scattering (SAXS) to determine if a lamellar structure is present in an dissolvable solid structure either in a conditioned, dry state or upon wetting after having been previously in a conditioned, dry state. Dissolvable solid structure are conditioned at a temperature of 23° C.±2.0° C. and a relative humidity of 40%±10% for a minimum of 12 hours prior to the test. Dissolvable solid structure conditioned as described herein are considered to be in a conditioned, dry state for the purposes of this invention. All instruments are calibrated according to manufacturer's specifications.

Dry Sample Preparation

To prepare a sample to be analyzed directly in the conditioned, dry state, a specimen of about 1.0 cm diameter disc is isolated from the center of a dissolvable solid structure and is loaded into a conventional SAXS solid sample holder with aperture diameter between 4 and 5 mm (Multiple specimen discs may be extracted from multiple dissolvable solid structures and stacked, if necessary, to ensure sufficient scattering cross-section.) The loaded sample holder is immediately placed in the appropriate instrument for data collection.

Wet Sample Preparation

Three samples are analyzed upon wetting from the dry, conditioned state. Specimens are extracted from dry, conditioned dissolvable solid structure and hydrated with water in order to achieve three separate preparations each possessing a different material-to-water mass ratio. The three different material-to-water mass ratios to be prepared are 1:5; 1:9; and 1:20. For each mass ratio, one or more specimens (as needed) 1 cm in diameter are extracted from the geometric centers of one or more dissolvable solid structure in the dry, conditioned state are hydrated with 23° C.±2.0° C. filtered deionized (DI) water in order to achieve the intended material-to-water mass ratio. Each of the three material/water mixtures (each corresponding to a different mass ratio) is stirred under low shear gently by hand at room temperature using a spatula until visibly homogenous. Each material/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate SAXS instrument and data are collected.

Testing and Analysis

Samples are tested using SAXS in 2-dimension (2D) transmission mode over an angular range in of 0.3° to 3.0° 2θ, to observe the presence and spacing of any intensity bands in the x-ray scatter pattern. The test is conducted using a SAXS instrument (such as the NanoSTAR, Bruker AXS Inc., Madison, Wisconsin, U.S.A., or equivalent). Conditioned, dry samples are analyzed under ambient pressure. Sealed liquid samples are analyzed in the instrument under vacuum. All samples are analyzed at a temperature of 23° C.±2.0° C. The x-ray tube of the instrument is operated sufficient power to ensure that any scattering bands present are clearly detected. The beam diameter is 550±50 µm. One suitable set of operating conditions includes the following selections: NanoSTAR instrument; micro-focus Cu x-ray tube; 45 kV and 0.650 mA power; Vantec 2K 2-Dimensional area detector; collection time of 1200 seconds; and distance between the sample and detector of 112.050 cm. The raw 2-D SAXS scattering pattern is integrated azimuthally to determine intensity (I) as a function of the scattering vector (q), which are expressed throughout this method units of reciprocal angstroms ($Å^{-1}$). The values for q are calculated by the SAXS instrument according to the following equation:

$$q = \frac{4\pi}{\lambda}\sin\theta$$

where:
2θ is the scattering angle; and
λ is the wavelength used.

For each integrated SAXS analyzed, the value of q in $A^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For a sample analyzed directly in the dry, conditioned state, if an intensity peak is present at $2q^* \pm 0.002$ $Å^{-1}$, the sample is determined to exhibit a lamellar structure, and the characteristic d-spacing parameter is defined as $2\pi/q^*$. If no intensity peak if present at $2q^* \pm 0.002$ $Å^{-1}$, the sample analyzed directly in the dry, conditioned state is determined to not exhibit a lamellar structure.

For a sample analyzed upon wetting from the dry, conditioned state, if an intensity peak is present at $2q^* \pm 0.002$ $Å^{-1}$, the sample is determined to exhibit a lamellar structure, and the characteristic d-spacing parameter is defined as $2\pi/q^*$. If no intensity peak is present at $2q^* \pm 0.002$ $Å^{-1}$, the sample is determined to not exhibit a lamellar structure. If a lamellar structure is determined to be present in at least any one of the three material/water ratios prepared, then this material is determined to exhibit a lamellar structure upon wetting. If no intensity peak is present at 2q*±0.002 Å$^{-1}$, in any of the three material/water ratios prepared, the material is determined to not exhibit a lamellar structure upon wetting.

Method for % Mass Loss Measured at 96 Hours

Place 500 g agglomerated particles in plastic bag with end open. Place plastic bag with Agglomerated Particle in beaker with open end up exposed to atmosphere. Allow to stand open for 96 hours. Weigh Agglomerated Particle. Calculate % loss.

Basis Weight Measurement

In general, basis weight of a material or article (including the dissolvable solid structure) is measured by first cutting the sample to a known area, using a die cutter or equivalent, then measuring & recording the weight of the sample on a top-loading balance with a minimum resolution of 0.01 g, then finally by calculating the basis weight as follows:

Basis Weight (g/m2)=weight of basis weight pad (g)

$$\text{Basis Weight} \left(\frac{g}{m^2}\right) = \frac{\text{Weight of pad (g)} \times 10,000 \frac{cm^2}{m^2}}{\text{area of pad } (cm^2)}$$

Suitable pad sample sizes for basis weight determination are >10 cm2 and should be cut with a precision die cutter having the desired geometry. If the dissolvable solid structure to be measured is smaller than 10 cm2, a smaller sampling area can be sued for basis weight determination with the appropriate changes to calculation.

In the present examples, basis weight was calculated based on the full dissolvable solid structure having a known area of 17.28 cm2. Thus, the basis weight calculation becomes:

$$\text{Basis Weight} \left(\frac{g}{m^2}\right) = \frac{\text{Weight of pad (g)} \times 10,000 \frac{cm^2}{m^2}}{17.28 \ cm^2}$$

Thickness (Caliper) Measurement

The present examples were measured using the Check-Line J-40-V Digital Material Thickness Gauge from Electromatic Equipment Co. (Cedarhurst, NY).

The sample (such as the dissolvable solid structure) is placed between a top and bottom plate of the instrument which has a top plate designed to apply a pressure of 0.5 kPa over a 25 cm2 area. The distance between the plates, to the nearest 0.01 mm, at the time of measurement is recorded as the thickness of the sample. The time of measurement is determined as the time at which the thickness in mm stabilizes or 5 seconds, whichever occurs first.

Equivalent methods are described in detail in compendial method ISO 9073-2, Determination of thickness for nonwovens, or equivalent.

Bulk Density (Density) Determination

Bulk Density is determined by calculation given a Thickness and Basis Weight of the sample (the solid dissolvable structure) (using methods as described above) according to the following:

$$\text{Bulk Density} \left(\frac{g}{cm^3}\right) = \frac{\text{Basis Weight of the pad} \left(\frac{g}{m^2}\right)}{\text{Thickness of the pad (mm)} \times 0.1 \frac{cm}{mm} \times 10,000 \frac{cm^2}{m^2}}$$

Method of Measuring the Footprint of a Dissolvable Solid Structure (or Article)

The footprint of the dissolvable solid structure can be measured by measuring the dimensions of its base so that the base area (that is, the footprint) can be calculated. For example, in the case in which the base of the article is a parallelogram having right angles, the length of the unequal sides of the base (A and B) are measured by a ruler and the area of the base (footprint) is calculated as the product A×B. In the case in which the base of the dissolvable solid structure is a square, the length of a side (C) is measured by a ruler and the area of the base (footprint) is calculated as the square C2. Other examples of shapes can include circle, oval, etc.

Hand Dissolution Test Method

Materials Needed

Dissolvable solid structures to be tested: 3-5 dissolvable solid structure s (finished product samples) are tested so that an average of the number of strokes for each if the individual dissolvable solid structure samples is calculated and recorded as the Average Hand Dissolution value for the dissolvable solid structure. For this method, the entire consumer saleable or consumer use dissolvable solid structure is tested. If the entire consumer saleable or consumer use dissolvable solid structure has a footprint greater than 50 cm$^2$, then first cut the dissolvable solid structure to have a footprint of 50 cm$^2$.

Nitrile Gloves
10 cc syringe
Plastic Weigh boat (~3 in×3 in)
100 mL Glass beaker
Water (City of Cincinnati Water or equivalent having the following properties: Total Hardness=155 mg/L as CaCO$_2$; Calcium content=33.2 mg/L; Magnesium content=17.5 mg/L; Phosphate content=0.0462 mg/L)
Water used is 7 gpg hardness and 40° C.+/−5° C.

Protocol

Add 80 mL of water to glass beaker. Add 300-500 ml of water to glass beaker.
Heat water in beaker until water is at a temperature of 40° C.+/−5° C.
Transfer 10 mL of the water from the beaker into the weigh boat via the syringe.

Within 10 seconds of transferring the water to the weigh boat, place dissolvable solid structure sample in palm of gloved hand (hand in cupped position in non-dominant hand to hold dissolvable solid structure sample).

Using dominant hand, add water quickly from the weigh boat to the dissolvable solid structure sample and allow to immediately wet for a period of 5-10 seconds.

Rub with opposite dominant hand (also gloved) in 2 rapid circular strokes.

Visually examine the dissolvable solid structure sample in hand after the 2 strokes. If dissolvable solid structure sample is completely dissolved, record number of strokes=2 Dissolution Strokes. If not completely dissolved, rub remaining dissolvable solid structure sample for 2 more circular strokes (4 total) and observe degree of dissolution. If the dissolvable solid structure sample contains no solid pieces after the 2 additional strokes, record number of strokes=4 Dissolution Strokes. If after the 4 strokes total, the dissolvable solid structure sample still contains solid pieces of un-dissolved dissolvable solid structure sample, continue rubbing remaining dissolvable solid structure sample in additional 2 circular strokes and check if there are any remaining solid pieces of dissolvable solid structure sample after each additional 2 strokes until dissolvable solid structure sample is completely dissolved or until reaching a total of 30 strokes, whichever comes first. Record the total number of strokes. Record 30 Dissolution Strokes even if solid dissolvable solid structure sample pieces remain after the maximum of 30 strokes.

Repeat this process for each of the additional 4 dissolvable solid structure samples.

Calculate the arithmetic mean of the recorded values of Dissolution Strokes for the 5 individual dissolvable solid structure samples and record as the Average Hand Dissolution Value for the dissolvable solid structure. The Average Hand Dissolution Value is reported to the nearest single Dissolution Stroke unit.

Fibrous Structures—Fiber Diameter

For fibrous Structures, the diameter of dissolvable fibers in a sample of a web is determined by using a Scanning Electron Microscope (SEM) or an Optical Microscope and image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in microns (μm). Several fibers are thus randomly selected across the sample of the web using the SEM or the optical microscope. At least two specimens from the web (or web inside a product) are cut and tested in this manner Altogether at least 100 such measurements are made and then all data are recorded for statistical analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micron diameter or %-submicron, for example. We denote the measured diameter (in microns) of an individual circular fiber as $d_i$.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $d_{num}$ $$\frac{\sum_{i=1}^{n} d_i}{n}$$

NON-LIMITING EXAMPLES

The compositions illustrated in the following Examples illustrate specific embodiments of the composition, but are not intended to be limiting thereof. Other modifications can be undertaken by the skilled artisan without departing from the spirit and scope of this invention. These exemplified embodiments of the composition as described herein provide enhanced conditioning benefits to the hair.

All exemplified amounts are listed as weight percents and exclude minor materials such as diluents, preservatives, color solutions, imagery ingredients, botanicals, and so forth, unless otherwise specified. All percentages are based on weight unless otherwise specified.

Conditioner Examples

| Raw Material | Ex 1 | Ex 2 | Ex 3 |
|---|---|---|---|
| Distilled Water | 2.1 | 1.9 | 1.6 |
| Behentrimonium Methosulfate [1] | 21.1 | 19.3 | 24.6 |
| Stearyl Alcohol | 46.4 | 42.4 | 43.6 |
| 1-Hexadecanol | 19.0 | 17.4 | 17.6 |
| Lauroyl Methyl Glucamide [2] | 0.0 | 8.7 | 8.6 |
| Polyvinyl pyrrolidone [3] | 4.2 | 3.9 | 3.9 |
| Amodimethicone [4] | 7.2 | 6.6 | 0.0 |
| Visible Homogeneity of Molten Composition | Y | Y | Y |
| Hand Dissolution Value | 20 | 6 | 6 |
| Presence of Lamellar Structure once hydrated (Y/N) | Y | Y | Y |

[1] Behentrimonium Methosulfate - IPA from Croda
[2] Glucotain Clean RM from Clariant
[3] PVP K120 from Ashland
[4] Amodimethicone from Momentive Performance Materials Conditioner Examples

| Raw Material | Ex 4 | Ex 5 | Ex 6 | Ex 7 | Ex 8 | Ex 9 | Ex 10 | Ex 11 | Ex 12 | Ex 13 | Ex 14 | Ex 15 | Ex 16 | Ex 17 |
|---|---|---|---|---|---|---|---|---|---|---|---|---|---|---|
| Distilled Water | 2.2 | 2.4 | 2.4 | 2.2 | 2.3 | 2.4 | 2.4 | 2.2 | 2.2 | 2.4 | 2.2 | 2.4 | 2.4 | 2.4 |
| Behentrimonium Methosulfate [1] | 19.4 | 3.9 | 3.9 | 31.0 | 3.9 | 31.0 | 31.0 | 31.0 | 3.9 | 3.9 | 31.0 | 31.0 | 3.9 | 19.3 |
| Stearyl Alcohol | 42.7 | 51.9 | 56.5 | 35.9 | 48.4 | 39.3 | 32.4 | 29 | 60.0 | 45.5 | 14.2 | 16.5 | 31.7 | 23.2 |
| 1-Hexadecanol | 17.5 | 21.8 | 21.8 | 15.5 | 20.4 | 16.8 | 14.1 | 12.8 | 23.4 | 17.4 | 21.8 | 25.2 | 51.5 | 36.8 |
| Lauroyl Methyl Glucamide [2] | 8.7 | 11.5 | 2.0 | 2.0 | 11.6 | 2.0 | 11.6 | 11.6 | 2.0 | 17.4 | 17.4 | 11.5 | 2.0 | 8.7 |
| Polyvinyl pyrrolidone [3] | 3.9 | 2.9 | 7.8 | 7.8 | 7.8 | 2.9 | 2.9 | 7.8 | 2.9 | 7.8 | 7.8 | 7.8 | 2.9 | 4.0 |
| Amodimethicone [4] | 5.6 | 5.6 | 5.6 | 5.6 | 5.6 | 5.6 | 5.6 | 5.6 | 5.6 | 5.6 | 5.6 | 5.6 | 5.6 | 5.6 |
| Visible Homogeneity of Molten Composition | Y | Y | Y | Y | Y | Y | Y | Y | Y | Y | Y | Y | Y | Y |
| Fiber Formation | Y | Y | Y | Y | Y | Y | Y | Y | Y | Y | Y | Y | Y | Y |

[1] Behentrimonium Methosulfate-IPA from Croda
[2] Glucotain Clean RM from Clariant
[3] PVP K120 from Ashland
[4] Amodimethicone from Momentive Performance Materials Conditioner Examples

| Raw Material | Ex 18 | Ex 19 | Ex 20 | Ex 21 | Ex 22 | Ex 23 | Ex 24 |
|---|---|---|---|---|---|---|---|
| Distilled Water | 2.4 | 2.4 | 2.4 | 2.4 | 2.4 | 2.4 | 2.4 |
| Stearamidopropyl Dimethylamine [1] | 0.0 | 0.0 | 0.0 | 15.5 | 15.5 | 19.4 | 31.0 |
| Behenamidopropyl Dimethylamine [2] | 31.0 | 31.0 | 31.0 | 0.0 | 0.0 | 0.0 | 0.0 |
| Palmitic Acid | 0.0 | 0.0 | 0.0 | 0.0 | 0.0 | 0.0 | 9.4 |
| Stearyl Alcohol | 35.9 | 39.3 | 32.4 | 45.6 | 44.9 | 42.7 | 26.4 |
| 1-Hexadecanol | 15.5 | 16.9 | 14.1 | 18.4 | 18.1 | 17.5 | 11.7 |
| Lauroyl Methyl Glucamide [3] | 1.9 | 1.9 | 11.6 | 8.7 | 8.7 | 8.7 | 8.7 |
| Polyvinyl pyrrolidone [4] | 7.8 | 2.9 | 2.9 | 3.9 | 4.9 | 3.9 | 4.9 |
| Amodimethicone [5] | 5.6 | 5.6 | 5.6 | 5.6 | 5.6 | 5.6 | 5.6 |
| Visible Homogeneity of Molten Composition | Y | Y | Y | Y | Y | Y | Y |
| Fiber Formation | Y | Y | Y | Y | Y | Y | Y |

[1] Stearamidopropyl Dimethylamine from Croda
[2] Behenamidopropyl Dimethylamine from Croda
[3] Glucotain Clean RM from Clariant
[4] PVP K120 from Ashland
[5] Amodimethicone from Momentive Performance Materials Negative Examples

| Raw Material | Comp Ex 1 | Comp Ex 2 | Comp Ex 3 | Comp Ex 4 | Comp Ex 5 | Comp Ex 6 | Comp Ex 7 | Comp Ex 8 | Comp Ex 9 |
|---|---|---|---|---|---|---|---|---|---|
| Distilled Water | 2.4 | 2.4 | 0.0 | 0.0 | 0.0 | 0.0 | 0.0 | 0.0 | 0.0 |
| Behentrimonium Methosulfate [1] | 0.0 | 0.0 | 30.0 | 30.0 | 30.0 | 30.0 | 30.0 | 30.0 | 30.0 |
| Stearamidopropyl Dimethylamine [2] | 23.3 | 31.0 | 0.0 | 0.0 | 0.0 | 0.0 | 0.0 | 0.0 | 0.0 |
| Stearyl Alcohol | 39.1 | 33.1 | 40.0 | 40.0 | 40.0 | 40.0 | 40.0 | 40.0 | 40.0 |
| 1-Hexadecanol | 16.4 | 14.4 | 20.0 | 20.0 | 20.0 | 20.0 | 20.0 | 20.0 | 20.0 |
| Lauroyl Methyl Glucamide [3] | 8.7 | 8.7 | 0.0 | 0.0 | 0.0 | 0.0 | 0.0 | 0.0 | 0.0 |
| Polyvinyl pyrrolidone [4] | 4.9 | 4.9 | 0.0 | 0.0 | 0.0 | 0.0 | 0.0 | 0.0 | 0.0 |
| PEO N60K | 0.0 | 0.0 | 10.0 | 0.0 | 0.0 | 0.0 | 0.0 | 0.0 | 0.0 |
| Polyacrylic acid [5] | 0.0 | 0.0 | 0.0 | 10.0 | 0.0 | 0.0 | 0.0 | 0.0 | 0.0 |
| Polyacrylamide [6] | 0.0 | 0.0 | 0.0 | 0.0 | 10.0 | 0.0 | 0.0 | 0.0 | 0.0 |
| PolyIsobutylene [7] | 0.0 | 0.0 | 0.0 | 0.0 | 0.0 | 10.0 | 0.0 | 0.0 | 0.0 |
| Polyacrylic acid copolymer [8] | 0.0 | 0.0 | 0.0 | 0.0 | 0.0 | 0.0 | 10.0 | 0.0 | 0.0 |
| Carboxy methyl cellulose [9] | 0.0 | 0.0 | 0.0 | 0.0 | 0.0 | 0.0 | 0.0 | 10.0 | 0.0 |
| Polyethylene Glycol 4000 | 0.0 | 0.0 | 0.0 | 0.0 | 0.0 | 0.0 | 0.0 | 0.0 | 10.0 |
| Amodimethicone [10] | 5.6 | 5.6 | 0.0 | 0.0 | 0.0 | 0.0 | 0.0 | 0.0 | 0.0 |

-continued

| Raw Material | Comp Ex 1 | Comp Ex 2 | Comp Ex 3 | Comp Ex 4 | Comp Ex 5 | Comp Ex 6 | Comp Ex 7 | Comp Ex 8 | Comp Ex 9 |
|---|---|---|---|---|---|---|---|---|---|
| Visible Homogeneity of Molten Composition | N | N | N | N | N | N | N | N | N |
| Fiber Formation | N | N | N | N | N | N | N | N | N |

[1] Behentrimonium Methosulfate-IPA from Croda
[2] Stearamidopropyl Dimethylamine from Croda
[3] Glucotain Clean RM from Clariant
[4] PVP K120 from Ashland
[5] Polyacrylic acid 10,000 g/mol from Aldrich
[6] Hyper Floc NF221 from HyChem/SNF
[7] Polyisobutylene from Aldrich MW = 1.0 e6 g/mol
[8] Accusol 588 G from Dow
[9] Finnfix 2 from CP Kelco
[10] Amodimethicone from Momentive Performance Materials Examples/Combinations A. A dissolvable solid structure comprising:
  a. fibrous material comprising;
    1) a polymeric structurant;
    2) a high melting point fatty material having a carbon chain length C12-C22 or mixtures thereof, wherein the melting point is above 25 C; and
    3) a cationic surfactant; wherein the polymeric structurant has a weight average molecular weight of from about 10,000 to about 6,000,000 g/mol, and wherein the components of the fibrous material form a homogenous material when molten, and wherein a lamellar structure is formed upon addition of water to the dissolvable solid structure in the ratio of about 5:1.

B. A dissolvable solid structure according to paragraph A comprising:
  a. fibrous material comprising;
    1) from about 1 wt % to about 50 wt % of a polymeric structurant;
    2) from about 10 wt % to about 85 wt % of one or more high melting point fatty material having a carbon chain length C12-C22 or mixtures thereof, wherein the melting point is above 25 C;
    3) from about 1 wt % to about 60 wt % of a cationic surfactant; wherein the polymeric structurant has a weight average molecular weight of from about 10,000 to about 6,000,000 g/mol, and wherein the components of the fibrous material form a homogenous material when molten, and wherein a lamellar structure is formed upon addition of water to the dissolvable solid structure in the ratio of about 5:1.

C. The structure according to paragraphs A-B, further comprising from about 1 wt % to about 30 wt % of a dispersing agent.

D. The structure according to paragraph A-C, wherein the dispersing agent is selected from the group consisting of a surfactant from the nonionic class of alkyl glucamides, reverse alkyl glucamides, cocoamiodpropyl betaines, alkyl glucoside, triethanol amine, cocamide MEAs and mixtures thereof.

E. The structure according to paragraph A-D, having from about 10 wt % to about 50 wt % of cationic surfactant.

F. The structure according to paragraph A-E, having from about 20 wt % to about 40 wt % of cationic surfactant.

G. The according to paragraph A-F, having from about 1 wt % to about 30 wt % of polymeric structurant.

H. The structure according to paragraph A-G, having from about 1 wt % to about 10 wt % polymeric structurant.

I. The structure according to paragraph A-H, having from about 2 wt % to about 6 wt % of a polymeric structurant.

J. The structure according to paragraph A-I, wherein the fatty amphiphile is selected from the group consisting of a fatty alcohol and a blend of one or more fatty alcohols.

K. The structure according to paragraph A-J, wherein the fatty amphiphile is a fatty acid.

L. The structure according to paragraph A-K, wherein the fatty amphiphile is a fatty amide.

M. The structure according to paragraph A-L, wherein the fatty amphiphile is a fatty ester.

N. The structure according to paragraph A-M, wherein the cationic surfactant is quaternized ammonium salt.

O. The structure according to paragraph A-N, wherein the cationic surfactant is a tertiary amine.

P. The structure according to paragraph A-O, wherein the polymeric structurant is polyvinylpyrrolidone.

Q. The structure according to paragraph A-P, wherein the polymeric structurant is a polyvinylpyrrolidone copolymer.

R. The structure according to paragraph A-Q, wherein the polymeric structurant is polydimethylacrylamide.

S. The structure according to paragraph A-R, wherein the polymeric structurant is polydimethylacrylamide copolymer.

T. The structure according to paragraph A-S, wherein the polymeric structurant is hydroxyl propyl cellulose.

U. The Structure according to paragraph A-T, wherein the Dissolvable Solid Structure dissolves in less than about 30 strokes of the Hand Dissolution Method.

V. The Structure according to paragraph A-U, wherein the Dissolvable Solid Structure dissolves in less than about 20 strokes of the Hand Dissolution Method.

W. The Structure according to paragraph A-V, wherein the Dissolvable Solid Structure dissolves in less than about 15 strokes of the Hand Dissolution Method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid fibrous structure comprising a plurality of filaments wherein the filaments comprise:
   a. a polymeric structurant comprising a weight average molecular weight of from about 10,000 to about 6,000,000 g/mol; wherein the polymeric structurant is free of polyvinyl alcohol;
   b. a high melting point fatty material having a carbon chain length C12-C22 or mixtures thereof, wherein the melting point is above 25° C.; and
   c. a cationic surfactant;
   wherein the components of the filaments form a homogenous material when molten;
   wherein a lamellar structure is formed upon addition of water to the dissolvable solid structure in the ratio of about 5:1;
   wherein the plurality of filaments are inter-entangled or otherwise associated with one another to form the fibrous structure;
   wherein at least 50% of the filaments comprise a diameter of less than 150 microns.

2. The structure of claim 1, wherein the article exhibits rapid dissolution in less than about 30 strokes according to the Hand Dissolution Method.

3. The structure of claim 1, wherein the filaments comprise;
   a. from about 1 wt % to about 50 wt % of the polymeric structurant;
   b. from about 10 wt % to about 85 wt % of the high melting point fatty material; and
   c. from about 1 wt % to about 60 wt % of the cationic surfactant.

4. The structure of claim 3, further comprising from about 1 wt % to about 30 wt % of a dispersing agent.

5. The structure of claim 4, wherein the dispersing agent is chosen from the nonionic class of alkyl glucamides, reverse alkyl glucamides, cocoamidopropyl betaines, alkyl glucoside, triethanol amine, cocamide monoethanolamines (cocamide MEAs), or mixtures thereof.

6. The structure of claim 3, having from about 10 wt % to about 50 wt % of cationic surfactant.

7. The structure of claim 6, having from about 20 wt % to about 40 wt % of cationic surfactant.

8. The structure of claim 3, having from about 1 wt % to about 30 wt % of polymeric structurant.

9. The structure of claim 8, having from about 1 wt % to about 10 wt % polymeric structurant.

10. The structure of claim 3, wherein the high melting point fatty material is chosen from a fatty alcohol and a blend of one or more fatty alcohols.

11. The structure of claim 3, wherein the cationic surfactant is quaternized ammonium salt.

12. The structure of claim 3, wherein the cationic surfactant is a tertiary amine.

13. The structure of claim 3, wherein the polymeric structurant is chosen from polyvinylpyrrolidone, polyvinylpyrrolidone copolymer, polydimethylacrylamide, polydimethylacrylamide copolymer, or mixtures thereof.

14. The structure of claim 1, wherein the dissolvable solid structure dissolves in less than about 20 strokes of the Hand Dissolution Method.

15. The structure of claim 1, wherein the dissolvable solid structure dissolves in less than about 15 strokes of the Hand Dissolution Method.

16. The structure of claim 1, wherein the filaments comprise meltblown filaments.

17. The structure of claim 1, wherein at least 50% of the filaments comprise a diameter of less than 100 microns.

18. The structure of claim 1, wherein at least 50% of the filaments comprise a diameter of less than 10 microns.

19. A dissolvable solid fibrous structure comprising a plurality of filaments wherein the filaments comprise:
   d. from about 1 wt % to about 10 wt % of a polymeric structurant comprising a weight average molecular weight of from about 10,000 to about 6,000,000 g/mol; wherein the polymeric structurant is free of polyvinyl alcohol;
   e. from about 20 wt % to about 70 wt % of a high melting point fatty material;
   wherein the high melting point fatty material comprises cetyl alcohol, stearyl alcohol, behenyl alcohol, or a mixture thereof;
   f. from about 10 wt % to about 50 wt % of a cationic surfactant comprising behentrimonium methosulfate;
   wherein the components of the filaments form a homogenous material when molten,
   wherein a lamellar structure is formed upon addition of water to the dissolvable solid structure in the ratio of about 5:1;
   wherein the plurality of filaments are inter-entangled or otherwise associated with one another to form the fibrous structure;
   wherein at least 50% of the filaments comprise a diameter of less than 150 microns.

* * * * *